(12) United States Patent
Laird

(10) Patent No.: US 11,014,170 B2
(45) Date of Patent: May 25, 2021

(54) DRILL BIT

(71) Applicant: BREMAJEK HOLDINGS PTY LTD, Matraville (AU)

(72) Inventor: Ewen James Laird, Matraville (AU)

(73) Assignee: Bremajek Holdings PTY LTD

( * ) Notice: Subject to any disclaimer, the term of this patent is extended or adjusted under 35 U.S.C. 154(b) by 0 days.

(21) Appl. No.: 16/962,756

(22) PCT Filed: Jan. 15, 2019

(86) PCT No.: PCT/AU2019/050021
§ 371 (c)(1),
(2) Date: Jul. 16, 2020

(87) PCT Pub. No.: WO2019/140482
PCT Pub. Date: Jul. 25, 2019

(65) Prior Publication Data
US 2020/0353543 A1 Nov. 12, 2020

(30) Foreign Application Priority Data

Jan. 22, 2018 (AU) ................................ 2018900199

(51) Int. Cl.
*A61B 17/16* (2006.01)
*B23B 51/02* (2006.01)

(52) U.S. Cl.
CPC .......... *B23B 51/02* (2013.01); *A61B 17/1615* (2013.01)

(58) Field of Classification Search
CPC ............ A61B 17/1615; A61B 17/1617; A61B 17/162; B23B 51/02

(Continued)

(56) References Cited

U.S. PATENT DOCUMENTS

2013/0006248 A1 1/2013 Ellis
2013/0253521 A1 9/2013 Ellis
(Continued)

OTHER PUBLICATIONS

International Search Report and Written Opinion, as issued in connection with International Patent Application No. PCT/AU2019/050021, dated Feb. 15, 2019, (12 pages).

*Primary Examiner* — Si Ming Ku

(57) ABSTRACT

A drill bit (100) having a longitudinal axis (101) and to be rotated about the axis (101) in a drilling direction (102) to perform a drilling operation. The drill bit (100) comprises a body (120) having a longitudinal length with a proximal end (121) and a distal end (122). The body (120) has a diameter. A tapered tip (110) extends from the proximal end (121) and terminates in an apex (111) at an end of the drill bit (100). The drill bit (100) also comprises a plurality of flutes (140) with each flute (140) extending helically along the body (120) into the tip (110). The drill bit (100) also comprises a land (150) between each of the flutes (140) and extends to the tip (110). The drill bit (100) also comprises a plurality of tip faces (190) on the tip (110) and extends from a corresponding land (150) to the apex (111), where each of the tip faces (190) has a tip face leading edge (173) and a tip face trailing edge (174). Each of tip face leading edges (173) forms an intersection with an adjacent one of the flutes (140) to provide a plurality of primary cutting edges (175). In a tip cross-sectional plane extending perpendicular to the axis (101) through each of the primary cutting edges (175), each of the primary cutting edges (175) lies on a circle extending about the axis (101) and each of the tip face trailing edges (174) lies entirely within the circle. Each of the flutes (140) helically extends in an opposite direction to the drilling direction (102).

15 Claims, 37 Drawing Sheets

(58) Field of Classification Search
USPC .......................................................... 606/80
See application file for complete search history.

(56) References Cited

U.S. PATENT DOCUMENTS

| | | |
|---|---|---|
| 2013/0296886 A1 | 11/2013 | Green et al. |
| 2014/0277188 A1 | 9/2014 | Poulos |
| 2017/0274461 A1 | 9/2017 | Mabuchi et al. |

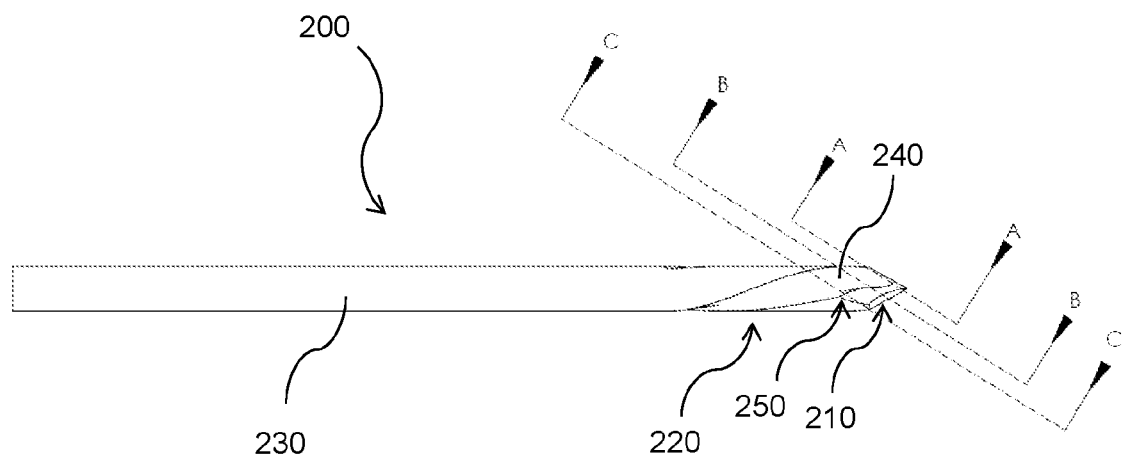
Fig. 10
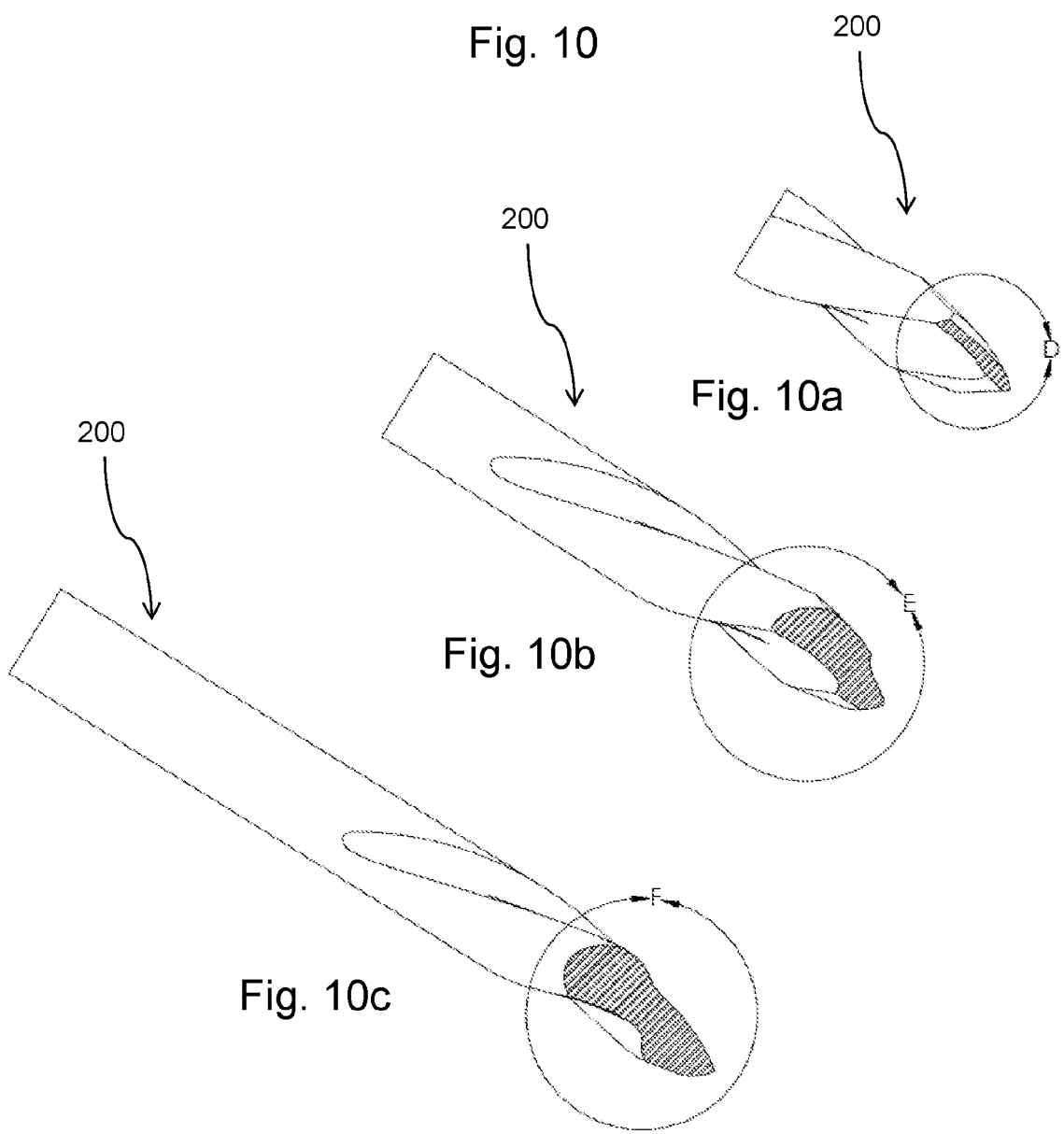
Fig. 10a
Fig. 10b
Fig. 10c

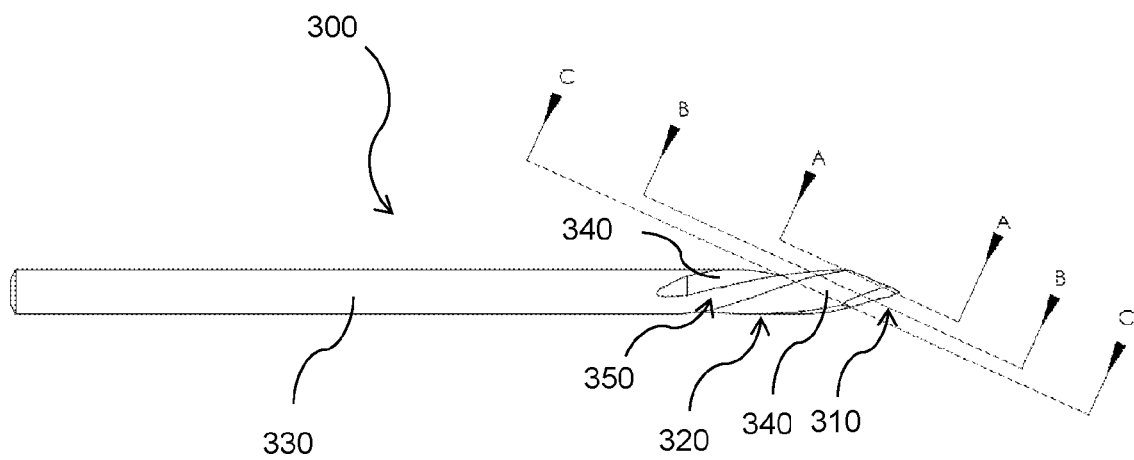
Fig. 15
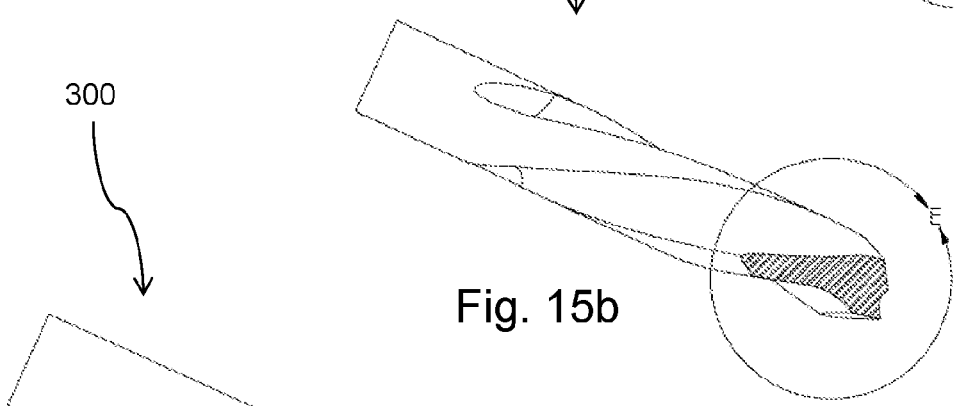
Fig. 15a
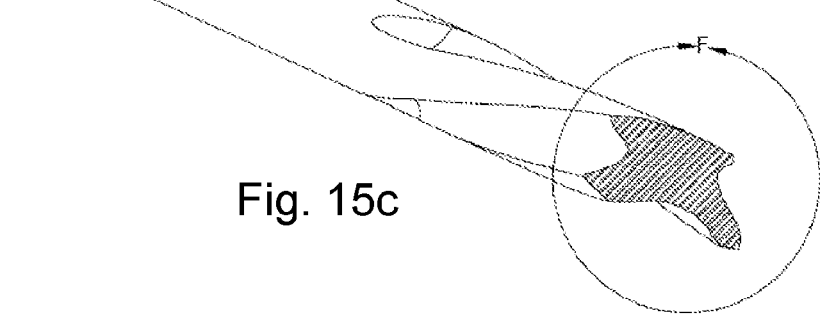
Fig. 15b
Fig. 15c

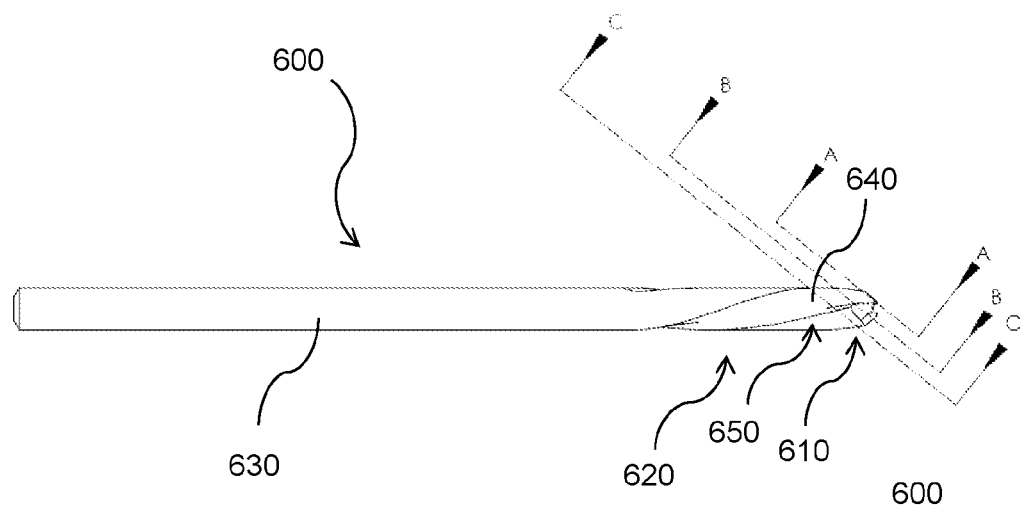
Fig. 30
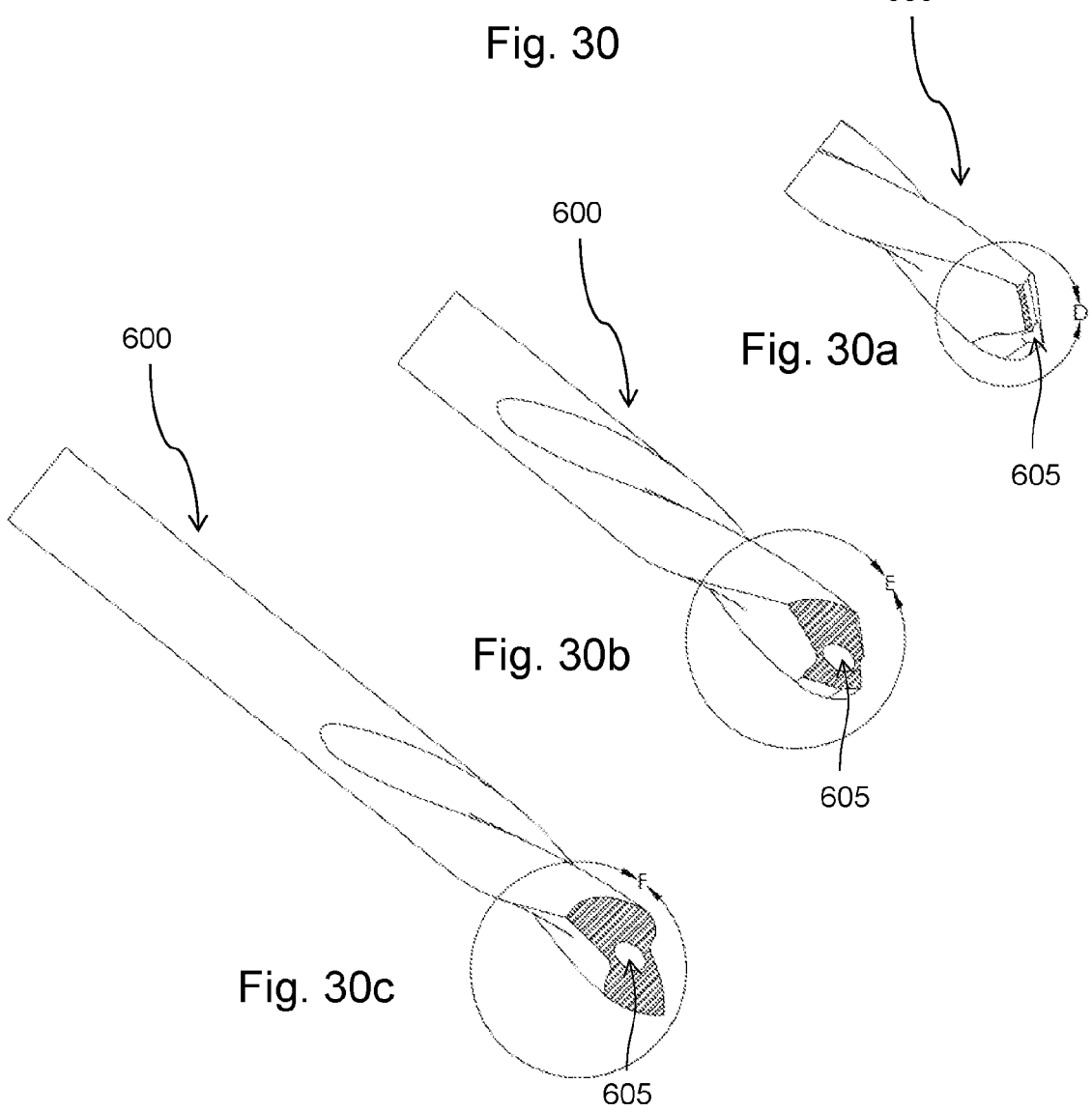
Fig. 30a
Fig. 30b
Fig. 30c

DRILL BIT

FIELD

The present invention relates to the field of drill bits and in particular relates to, but is not limited to, an orthopaedic drill bit.

BACKGROUND

Drill bits are traditionally formed from a rod/shaft of high strength metallic material by grinding two or more helical gulleys, known as flutes, into the side wall of the rod extending from the operative front end of the rod towards the rear end, leaving a cylindrical shank at the rear end of the rod. The flutes typically extend helically in a clockwise (or right-handed) direction when viewed from the rear of the shank. The flutes are separated by lands that define the full diameter of the rod.

The cutting end part of the drill bit, generally known as the tip or point, is formed by grinding the end region of the rod to provide a generally conical end part with end or tip faces extending from each land towards either a chiselled edge, for designs with two flutes, or a sharp apex for designs with three or more flutes. A primary cutting edge is defined by the junction between the leading edge of each of the tip faces and the adjacent trailing side wall of the adjacent flute. It is these primary cutting edges that cut material being drilled at the end of the drill hole. The shavings of swarf cut from the material pass along the flutes towards the rear of the drill bit, thereby creating room for more material to be cut or shaved and passed into and along the flutes for ejection from the rear end of the flutes.

In orthopaedic applications, typical orthopaedic drill bits produce shavings of bone swarf mixed with bone marrow, blood, plus other fluids and cells, which are ejected from the rear end of the flutes and which could form part of an autograft rather than be discarded. However; a lot of bone drilling is performed with minimal access through deep wounds, tubular drill guides or cannulae. Collecting and replacing the drilled bone, to form an autograft base for device fixation is therefore not practical or even possible in many cases. Device fixation, after drilling is often augmented with synthetic bone fillers, bone cements, donor graft material or allograft.

It is a well-known truth that the patients' own body material, in the form of an autograft, is far more acceptable from the body's perspective. Therefore, it can be seen as beneficial if the ejected bone swarf shavings are collected and reintroduced back into the drill hole with the intention to promote bone re-growth in and around the perimeter of the drill hole, and any fracture site, in order to provide improved purchase and stability for bone screws or other fixation devices. This is particularly the case with osteoporotic bone as it is often soft and frangible thereby requiring as much reinforcement as possible.

OBJECT OF THE INVENTION

It is an object of the present invention to substantially overcome or at least ameliorate the above disadvantage.

SUMMARY OF INVENTION

The present invention provides a drill bit having a longitudinal axis and to be rotated about the axis in a drilling direction to perform a drilling operation, the drill bit comprising:

a body having a longitudinal length with a proximal end and a distal end, the body having a diameter;

a tapered tip extending from the proximal end and terminating in an apex at an end of the drill bit;

a plurality of flutes, each flute extending helically along the body into the tip;

a land between each of the flutes and extending to the tip;

a plurality of tip faces on the tip and extending from a corresponding land to the apex, each of the tip faces having a tip face leading edge and a tip face trailing edge, each of the tip face leading edges forming an intersection with an adjacent one of the flutes to provide a plurality of primary cutting edges; and wherein in a tip cross-sectional plane extending perpendicular to the axis through each of the primary cutting edges, each of the primary cutting edges lies on a circle extending about the axis and each of the tip face trailing edges lies entirely within the circle, each of the flutes helically extending in an opposite direction to the drilling direction.

In one or more embodiments, a negative rake angle is defined at each primary cutting edge.

In one or more embodiments, each of the flutes have a volume, the total volume of each of the flutes being between about 55 to 65 percent of a volume of a solid cylinder having a diameter equal to the diameter of the body and a length equal to the longitudinal length of the body over which each of the flutes extend.

In one or more embodiments, the length of each of the flutes is about 5 to 10 times the diameter of the body.

In one or more embodiments, each of the tip faces is substantially planar.

In one or more embodiments, each of the tip faces is concavely curved about the axis towards the drilling direction.

In one or more embodiments, each of the tip faces comprises a forward tip face region extending from adjacent an end of each of the flutes to the apex and a rear tip face region extending from the forward tip face region to an adjacent the land, the second tip face region being separated by each of the flutes, wherein each of the tip faces extend along the rear tip face region and the forward tip face region to the apex, such that each of the tip faces meet at the apex to define a substantially pyramidal arrangement of a forward extremity of the tip.

In one or more embodiments, each of the tip faces comprises a primary facet extending along the rear tip face region and the forward tip face region to the apex and a secondary facet inclined relative to the primary facet and extending along the rear tip face region and the forward tip face region to the apex, such that the secondary facet and the primary facet meet at the apex to define the pyramidal arrangement of the forward extremity of the tip.

In one or more embodiments, the drill bit has two flutes.

In one or more embodiments, the drill bit has three flutes.

In one or more embodiments, in a cross-sectional plane extending perpendicular to the axis through the body adjacent the tip, each of the flutes subtends an arc of between about 125 to 135 degrees measured at a radially outer periphery of each of the flutes.

In one or more embodiments, in a cross-sectional plane extending perpendicular to the axis through the body adjacent the tip, each of the flutes subtends an arc of between about 100 to 110 degrees measured at a radially outer periphery of each of the flutes.

In one or more embodiments, the drill bit further comprises a hole extending longitudinally about the axis from one end of the drill bit to the other end of the drill bit, the hole being configured to receive a guide wire for positioning the drill bit.

In one or more embodiments, the drilling direction is a clockwise direction when viewed from the distal end toward the proximal end.

In one or more embodiments, the drill bit is an orthopaedic drill bit.

BRIEF DESCRIPTION OF DRAWINGS

Exemplary embodiments of the present invention will now be described, by way of example only, with reference to the accompanying drawings wherein:

FIG. 10 is a second front elevation view of the drill bit of FIG. 6;

FIGS. 10a through 10c are each perspective/fragmentary cross-sectional views of the drill bit of FIG. 6 taken at sections A-A to C-C of FIG. 10 respectively;

FIG. 15 is a second front elevation view of the drill bit of FIG. 11;

FIGS. 15a through 15c are each perspective/fragmentary cross-sectional views of the drill bit of FIG. 11 taken at sections A-A to C-C of FIG. 15 respectively;

FIG. 30 is a second front elevation view of the drill bit of FIG. 26;

FIGS. 30a through 30c are each perspective/fragmentary cross-sectional views of the drill bit of FIG. 26 taken at sections A-A to C-C of FIG. 30 respectively.

DESCRIPTION OF EMBODIMENTS

Figure 1:
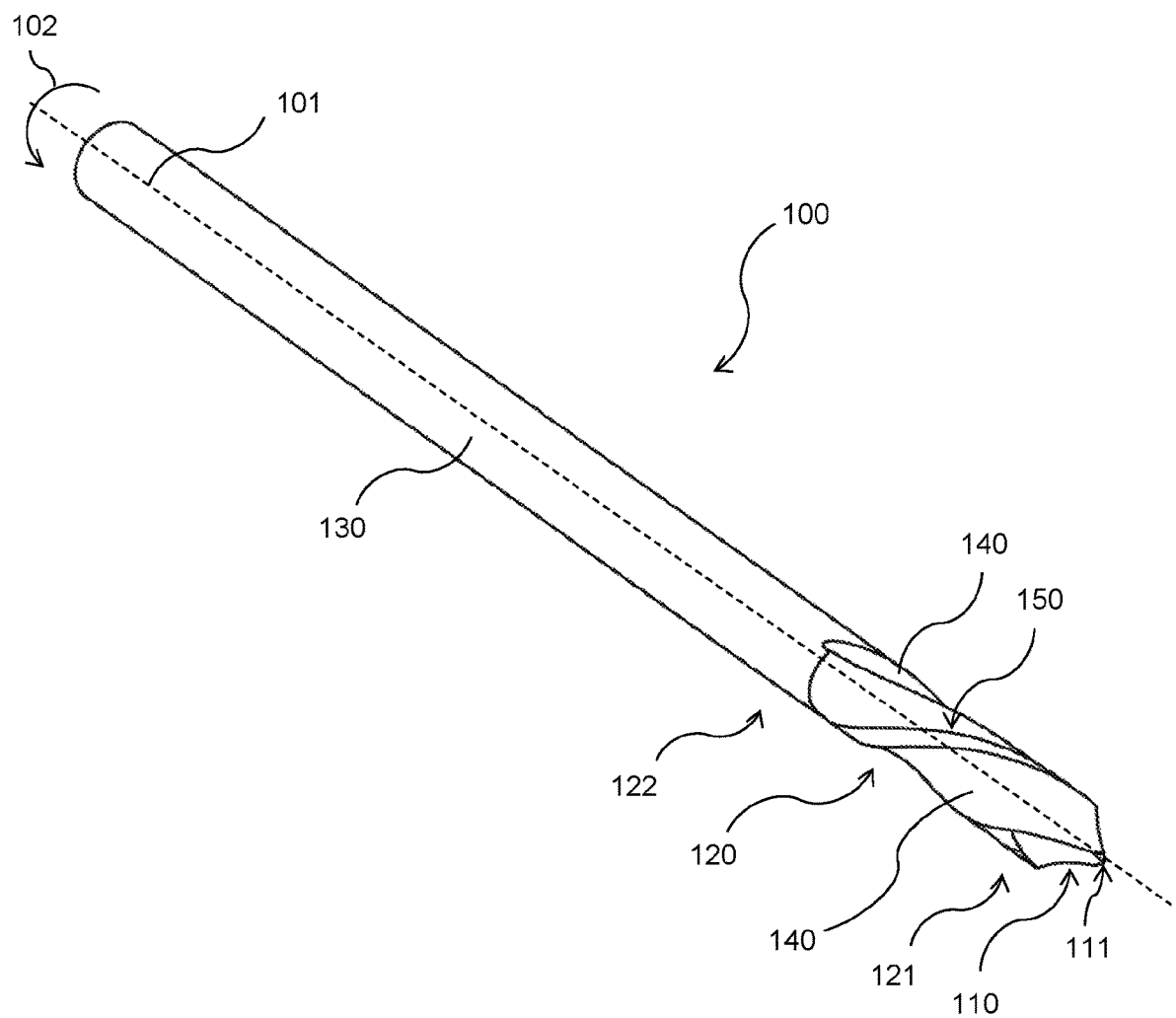
FIG. 1 is a perspective view of a drill bit according to a first embodiment of the invention.

A drill bit 100 according to a first embodiment is depicted in FIGS. 1 through 5 of the accompanying drawings. The drill bit 100 has a longitudinal axis 101 and is intended to be rotated about the axis 101 in a drilling direction 102 to perform a drilling operation. The drill bit 100 has a body 120 having a longitudinal length with a proximal end 121 and a distal end 122. A tapered tip 110 extends from the proximal end 121 of the body 120 and terminates in an apex 111 at a front, operative end of the drill bit 100. The distal end 122 of the body 120 preferably comprises a shank 130 which is configured to be received within the chuck of a drill in the usual way, and will typically be cylindrical although it may be hexagonal in cross-section or any other suitable shape. Two flutes 140 are formed in the drill bit 100 and each extend helically from adjacent the shank 130 along the body 120 into the tip 110. Each of the flutes 140 extends into the tip 110 towards the apex 111, but finishes just short of the apex 111 as a result of the tapering of the tip 110.

In the embodiment depicted, the drill bit 100 is configured to be rotated during the drilling operation in a clockwise direction when viewed from the distal end 122 of the body 120. This direction is also referred to as a right-handed direction. Throughout this specification, various features of the drill bit will be referred to as "leading" or "trailing", with this terminology indicating features that lead or trail respectively as the drill bit rotates in the intended manner. Alternate embodiments are envisaged where the drill bit is configured to be rotated in a counter-clockwise or left-handed direction during a drilling operation. In either form, the direction of intended rotation during a drilling operation may be referred to as a first-handed direction or a drilling direction.

Figure 2:
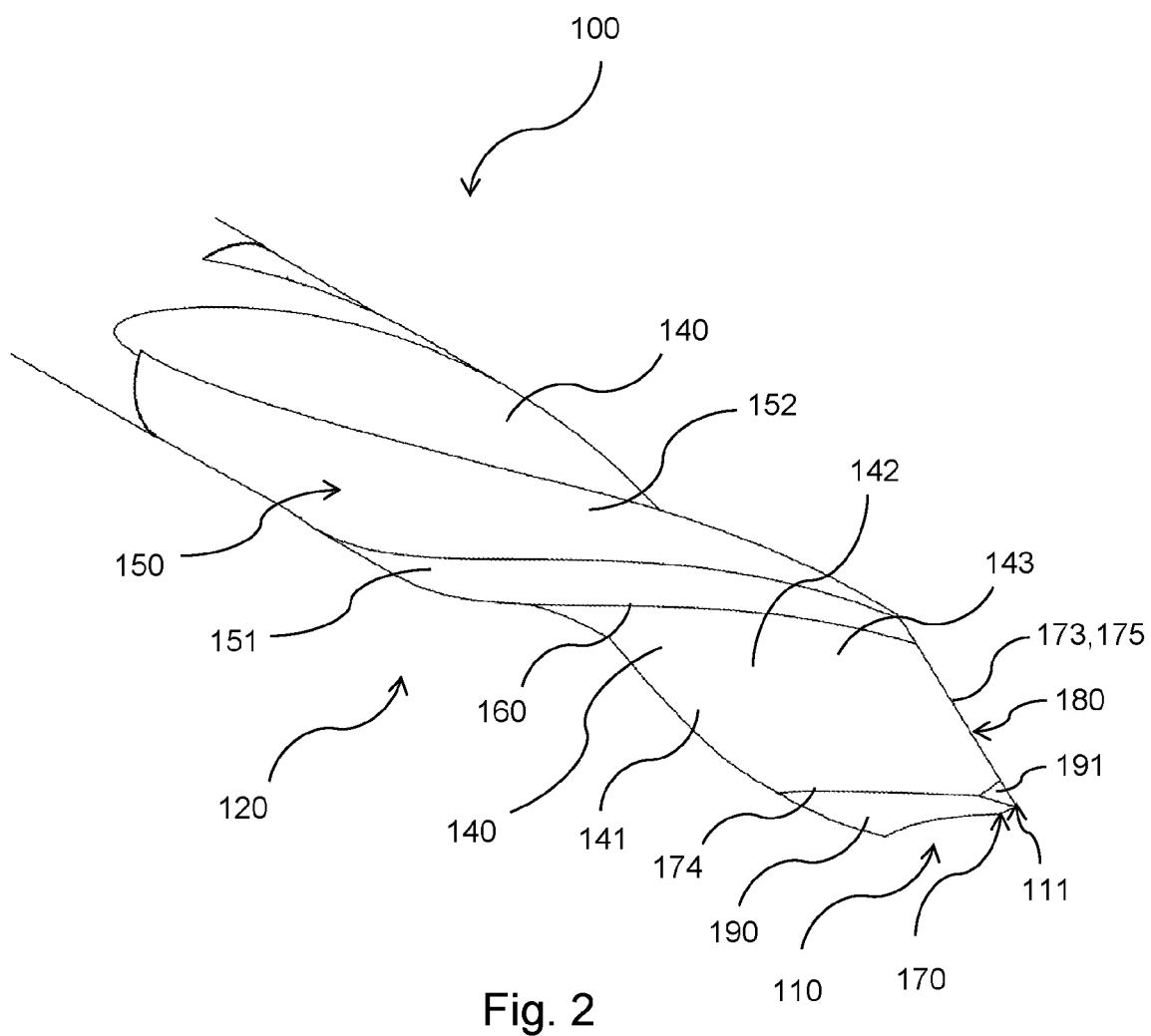
FIG. 2 is an enlarged perspective view of the tip of the drill bit of FIG. 1.
Figure 3:
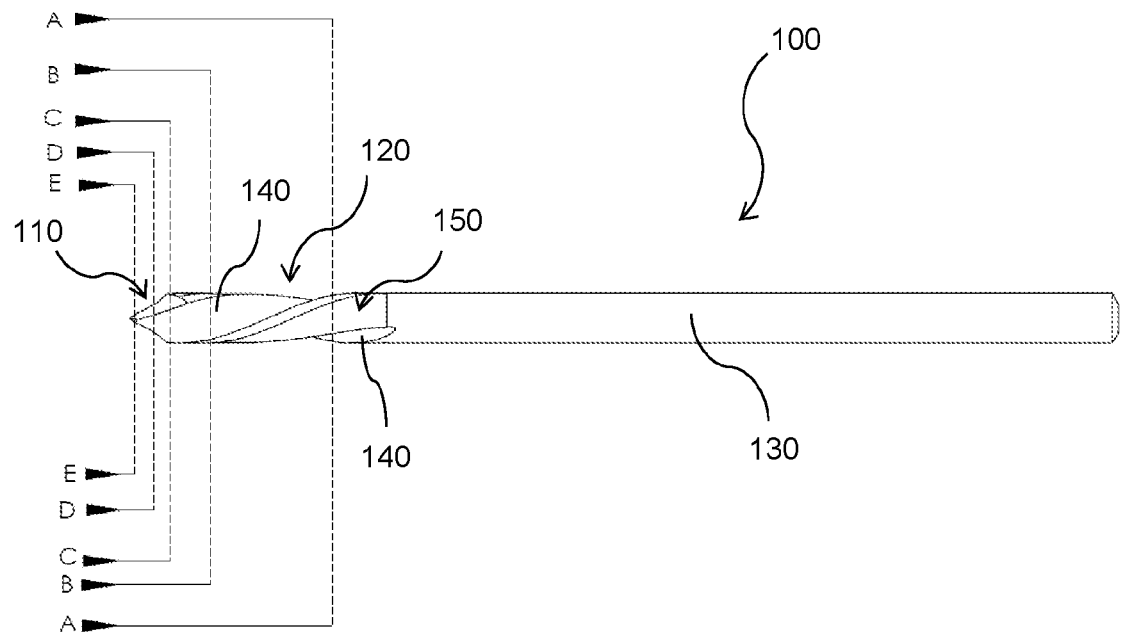
FIG. 3 is a first front elevation view of the drill bit of FIG. 1.
Figure 3A:
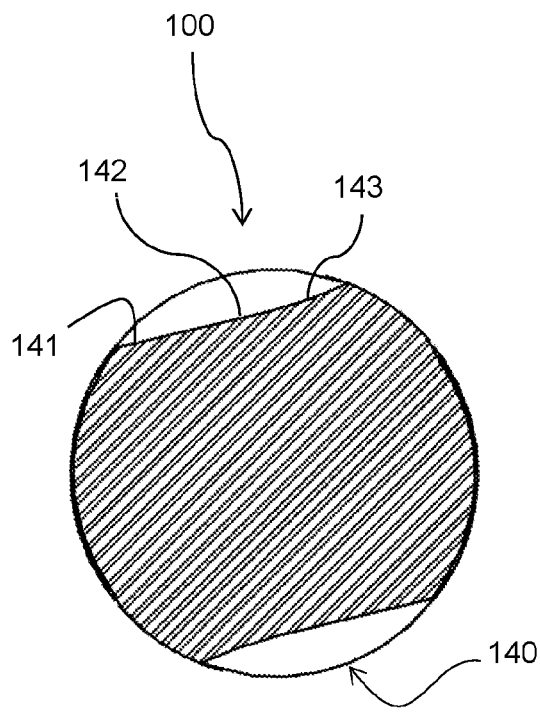
FIGS. 3a through 3e are each cross-sectional views of the drill bit of FIG. 1 taken at sections A-A to E-E of FIG. 3 respectively.

Referring to FIG. 2, each of the flutes 140 has a flute leading side wall 141 (which faces against the intended direction of rotation) and a flute trailing side wall 143 (which faces in the intended direction of rotation). The flute leading side wall 141 is joined to the flute trailing side wall 143 by way of a flute base 142 located therebetween. As best depicted in the cross-sectional views of FIGS. 3a and 3b, the flute leading side wall 141, flute base 142 and flute trailing side wall 143 effectively form a smooth continuous surface. The form of the flutes 140 is also relatively flat. The flutes 140 are each formed with a helix angle, which may typically be about 16° for the embodiments depicted, although the helix angle may be adjusted as desired for different applications. Typical helix angles will be between 5° and 20°, more typically between 12° and 18°. The flute bases 142 have a slight taper which may typically be about 6 degrees with respect to the axis 101 of the drill bit 100, reducing the depth of the flutes 140 towards the shank 130. Typical helix tapers will be between 3 to 6 degrees. The length of each of the flutes 140 is typically about 5 to 10 times the overall diameter of the drill bit 100. In the first embodiment, the volume of each of the flutes 140 is approximately equal to 30% of the volume of the same length of the drill bit 100 without each of the flutes 140 such that the total flute volume (of the two flutes) is approximately equal to 60% of the volume of the drill bit 100 without the flutes 140. That is, the total volume of the flutes 140 is approximately equal to 60% of the volume of a solid cylinder having a diameter equal to the overall diameter of the drill bit 100 and a length equal to a longitudinal extent of the drill bit 100 over which the flutes 140 extend. Typically, the total volume of the flutes 140 is about 55 to 65% of the volume of the drill bit 100 without the flutes 140. This percentage would increase with the helix taper. In alternate embodiments, it is envisaged that the same flute length and total flute volume will typically apply irrespective of the number of flutes (within about +/−5%).

Figure 3B:
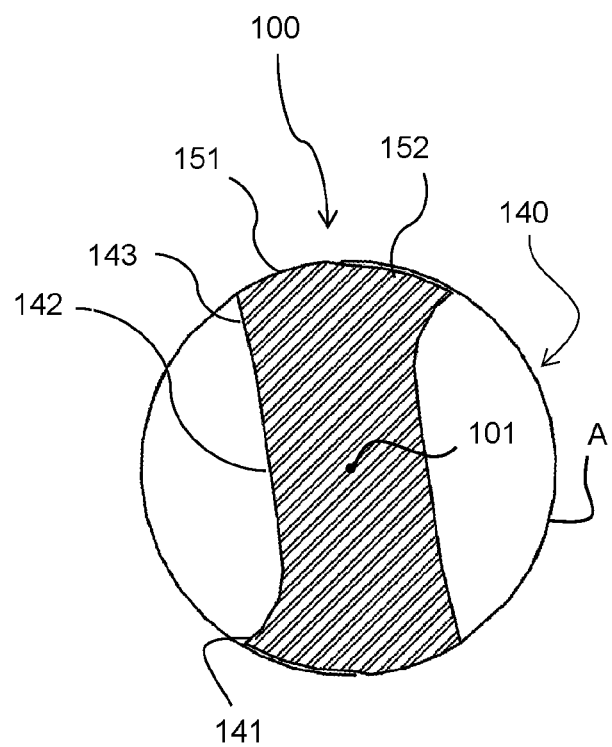
Figure 3C:
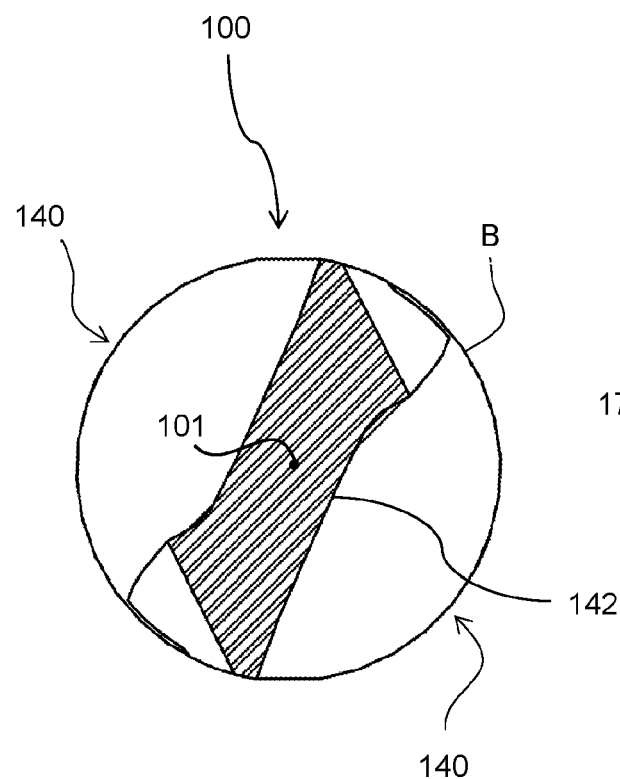

As best depicted in the cross-sectional view of FIG. 3c, each of the flutes 140 subtends an arc of typically about 125 to 135 degrees measured on a circle B extending about the axis 101 of the drill bit 100. This angle tends towards 0 degrees as the helix taper pushes the base 142 of each of the flutes 140 towards the outer diameter of the body 120.

The helix of the flutes 140 is orientated such that the rear end of each flute 140 leads the front end as the drill bit 100 rotates in the intended clockwise or right-handed direction (that is, the first-handed direction). In this regard, each of the flutes 140 helically extends in a counter-clockwise direction, as it advances towards the apex 111 of the drill bit 100, when viewed from the rear of the shank 130 thereby opposing the clockwise or right-handed direction of rotation of the drill bit 100. This opposing direction may be referred to as a second-handed direction opposing the first-handed direction. In alternate embodiments where the drill bit 100 is configured to be rotated in a counter-clockwise or left-handed direction during a drilling operation, the flutes 140 are orientated in a clockwise or right-handed direction.

A body land 150 is defined between each of the flutes 140. As best depicted in FIG. 2, each body land 150 has a leading body land margin 151 which adjoins the adjacent flute trailing side wall 143 of the flute 140 directly leading the body land 150, defining a secondary cutting edge 160. Each body land 150 also has a body land relief 152 which extends from the body land margin 151 towards the adjacent flute leading side wall 141 of the flute 140 directly trailing the body land 150.

The body land margin 151 constitutes a part cylindrical portion of the body land 150 which is not ground away from the cylindrical shaft from which the drill bit 100 is formed. The body land margin 151 has a width (measured in a cross-sectional plane) of about 0.5 mm to 1 mm in the embodiment depicted, however, it is envisaged that the body land margin 151 may have a minimal width, effectively defined by the secondary cutting edge 160. As best depicted in FIG. 3b, the body land margins 151 each lie on a circle A extending about the axis 101 and having a diameter equal to the overall diameter of the drill bit 100. The body land relief 152 of each body land 150 are ground away from the cylindrical shaft from which the drill bit 100 is formed. Accordingly, at any cross-sectional plane extending perpendicular to the axis 101 through the body lands 150, each body land relief 152 lies entirely within the circle A. The body land relief 152 provides a clearance between the bulk of the body land 150 and the wall of the hole being drilled, thereby reducing drill bit drag in the usual manner. It is, however, envisaged that the body 120 may be formed without any body land relief 152.

Figure 3D:
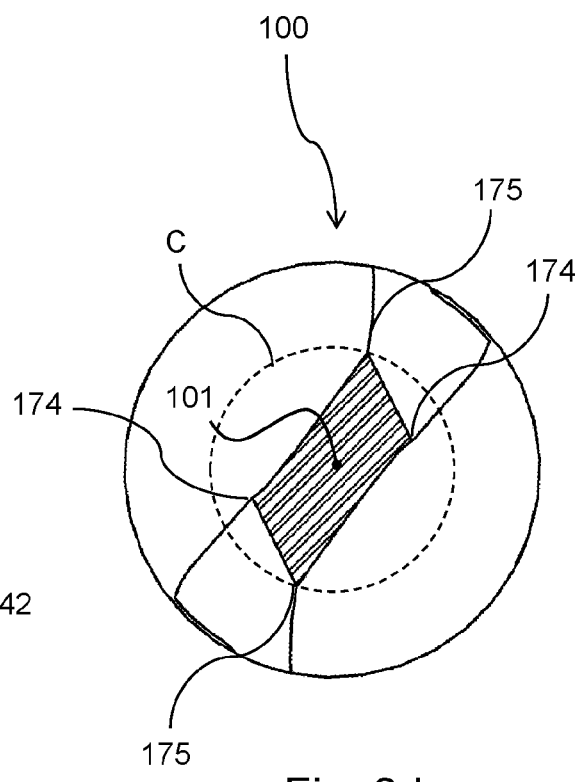
Figure 4:
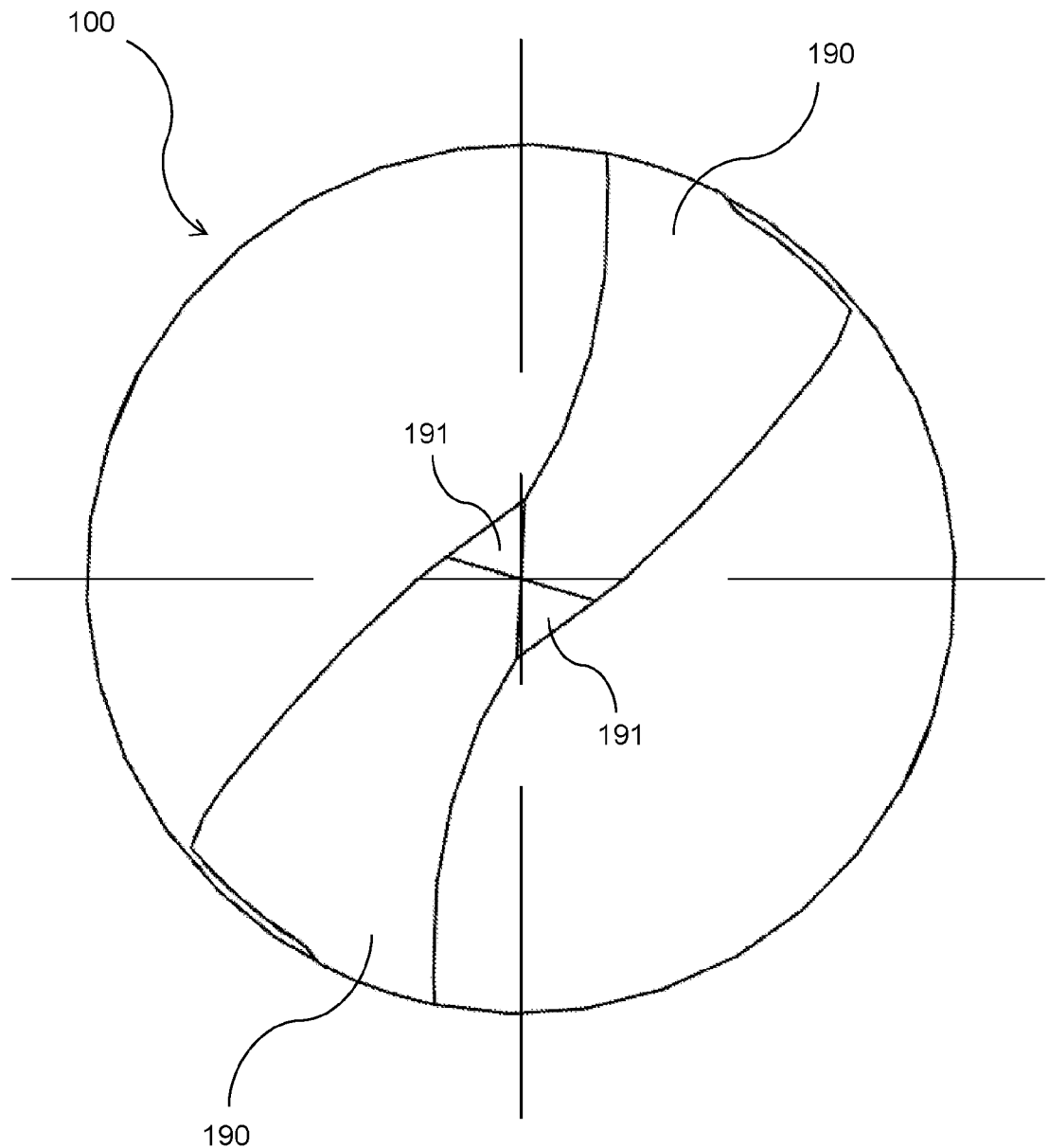
FIG. 4 is an enlarged end elevation view of the drill bit of FIG. 1.
Figure 5:
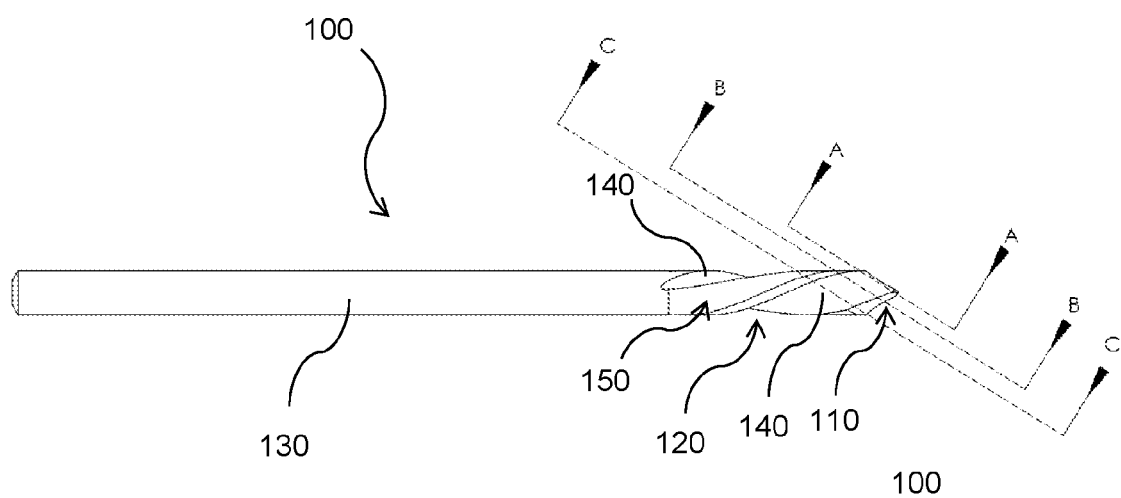
FIG. 5 is a second front elevation view of the drill bit of FIG. 1.
Figure 5A:
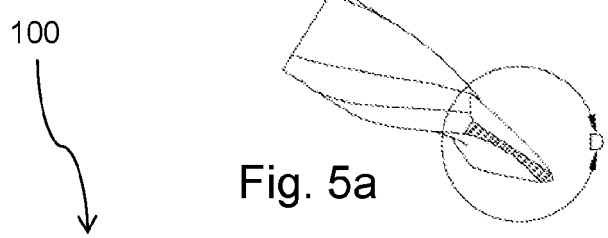
FIGS. 5a through 5c are each perspective/fragmentary cross-sectional views of the drill bit of FIG. 1 taken at sections A-A to C-C of FIG. 5 respectively.
Figure 5B:
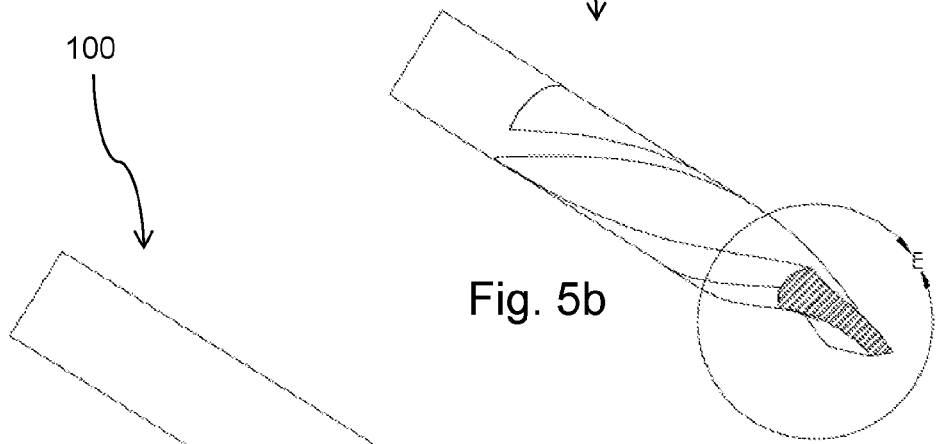
Figure 5C:
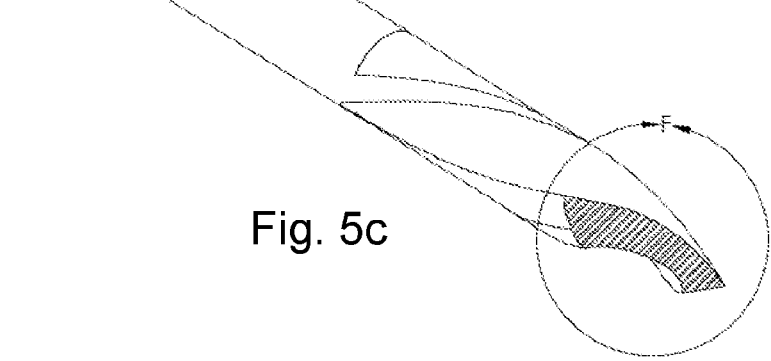
Figure 6:
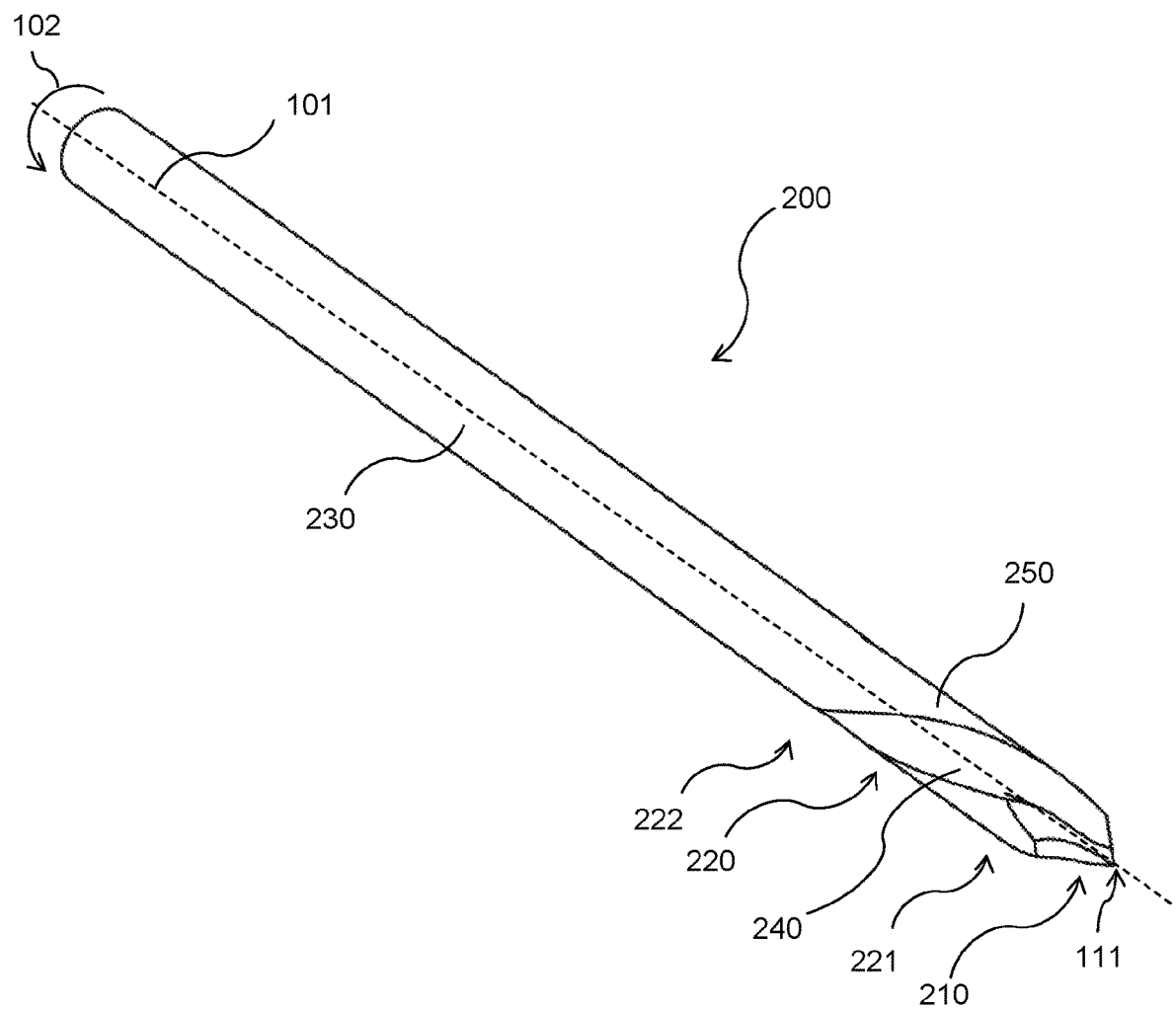
FIG. 6 is a perspective view of a drill bit according to a second embodiment of the invention.

As best depicted in FIGS. 2 and 4, two tip faces 190 are defined on the tip 110 and each extend from a corresponding body land 150 to the apex 111. Each of the tip faces 190 has a tip face leading edge 173 and a tip face trailing edge 174. Each of the tip faces 190, at the tip face leading edge 173, forms an intersection with an adjacent flute 140 to define a primary cutting edge 175. In substantially any tip cross-sectional plane extending perpendicular to the axis 101 through the primary cutting edges 175 (as best depicted in the cross-sectional view of FIG. 3d) each of the primary cutting edges 175 lies on a circle C extending about the axis 101 and each of the tip face trailing edges 174 lies entirely within the circle C.

Figure 31:
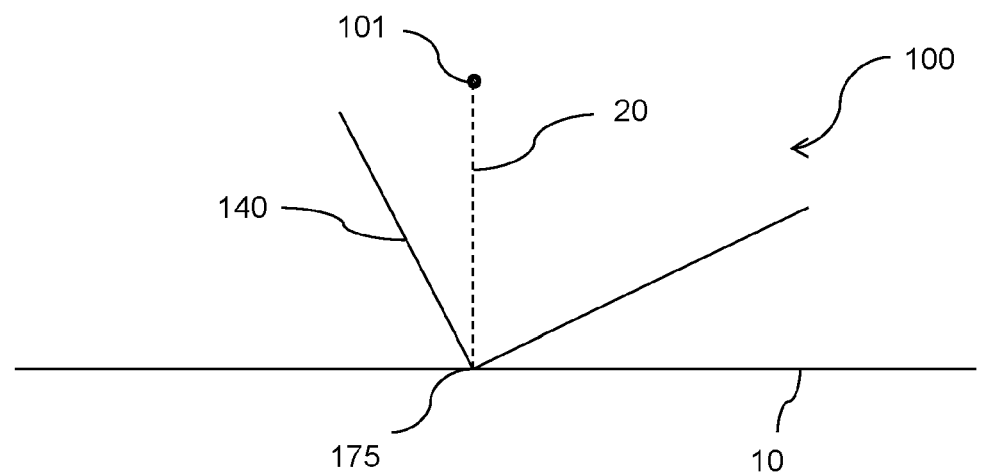
FIG. 31 is a schematic diagram of the rake angle formed by the drill bit of each of FIGS. 1, 6, 11, 16, 21 and 26.

FIG. 31 provides a simplified representation of the relationship between one of the primary cutting edges 175 and a bone surface 10 being drilled. FIG. 31 depicts a cross-section of the cutting site taken in a plane transverse to the primary cutting edge 175 and simplified to show the longitudinally extending axis 101 oriented perpendicular to the primary cutting edge 175. The bone surface 10 being cut is also simplified to be depicted as planar (whereas the bone surface being cut, within the hole being drilled, will in fact be arcuate). At the primary cutting edge 175, the bone surface 10 will be approximately perpendicular to a radius 20 extending from the axis 101 to the primary cutting edge 175. The surface of the flute 140 at the primary cutting edge 175, defining the cutting face, is inclined so as to subtend an acute included angle between the bone surface 10 and the cutting face, thereby defining a negative rake angle at the primary cutting edge 175. Typically, the negative rake angle will be about 10 to 20 degrees. The negative rake angle is facilitated by the flutes 140 extending in the opposing left-handed direction, such that the flutes 140 are each oriented in the tip 110 substantially perpendicular to the respective adjacent primary cutting edge 175, with the primary cutting edge 175 largely being defined by the intersection between the forward end of the flute 140 and the adjacent trailing tip face 190 at the tip face leading edge 173. This can be contrasted with a conventional drill bit where the flute extends in the same direction as the direction of rotation during the drilling operation, in which the flutes are each oriented in the tip substantially parallel to the respective adjacent primary cutting edge, with the primary cutting edge largely being defined by the intersection between the trailing side wall of the flute and the adjacent trailing tip face, typically resulting in a positive or zero rake angle. A positive rake angle is typically not suitable for cutting live bone since the positive rake angle makes the drill bit overly aggressive and will tend to grab and dive into the bone. This can be dangerous for the patient and hard to control for the surgeon. Most bone drills have a secondary cutting edge ground into the flute to create a slight negative rake angle to overcome this. The drill bit 100 provides a more negative rake angle than is typical. However, a negative rake angle of about 30 degrees is the standard for all trocar-style cutting tips.

This negative rake angle ensures the drill bit 100 performs a scraping motion across the cutting surface rather than a sharp, aggressive cut. Consequently, the drill bit 100 may not be suitable for drilling through hard, healthy, compact bone; however, the drill bit 100 is not intended for this purpose but is rather intended for drilling through osteoporotic bone which is typically soft and frangible.

Referring again to FIG. 2, each of the tip faces 190 of the drill bit 100 has two regions, being a forward tip face region 170 and a rear tip face region 180. Each forward tip face region 170 extends from adjacent the end of the flutes 140 to the apex 111 and constitutes the solid forward end of the tip 110. Each rear tip face region 180 constitutes the region extending from the forward tip face region 170 to the forward end of the adjacent body land 150. The rear tip face regions 180 are each separated by one of the flutes 140.

Figure 3E:
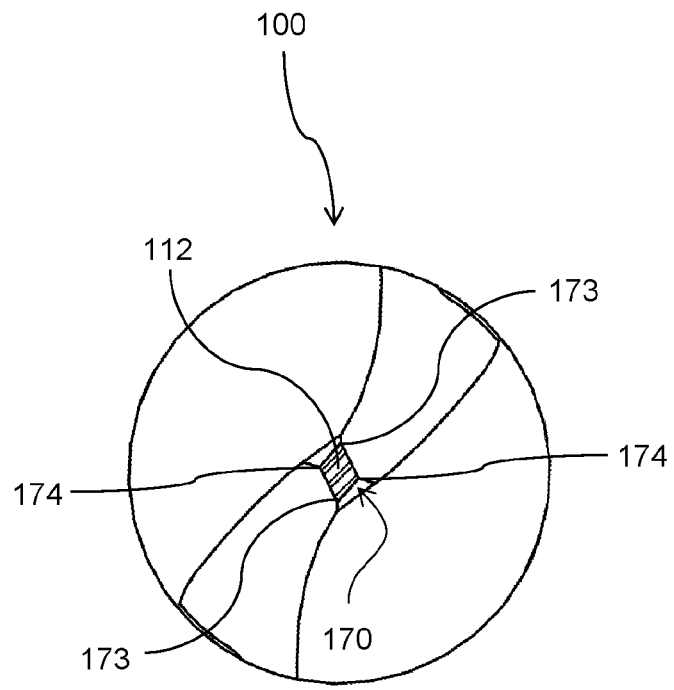

As best depicted in FIGS. 2 and 4, each tip face 190 comprises a chamfer 191 located in the forward tip face region 170. Without each of these chamfers, each of the tip faces 190 would inevitably define a chisel edge resulting from the configuration of their two planar faces. These chamfered portions of the tip 110 may form the basis of a relief section. In this regard, the forward tip face region 170 defines a substantially diamond-shaped pyramid of the forward extremity of the tip 110 where each of the opposing pyramidal edges of the pyramid form included angles. As best depicted in the cross-sectional view of FIG. 3e, this translates to a parallelogram 112 in cross-section where one diagonal of the parallelogram 112 is greater than the other. Those corners of the parallelogram 112 which are located on the longer diagonal of the parallelogram 112 lie on one of the respective tip face leading edges 173 in the forward tip face region 170, thereby defining a negative rake angle at the tip face leading edge 173 of the apex 111. Those corners of the parallelogram 112 which are located on the shorter diagonal of the parallelogram 112 lie on one of the respective tip face trailing edges 174 in the forward tip face region 170. The intersection of each of the pyramidal edges of the pyramid defines a sharp point at the apex 111 as best depicted in FIG. 2.

The tip faces 190 define an included drill point angle, which is about 60° in the embodiment depicted, although the drill point angle may be altered as desired to suit the material to be drilled.

The drill bit 100 will typically be formed of stainless steel when configured for use as an orthopaedic drill bit, but other suitable high strength metallic materials may be utilised as desired. The overall diameter of the drill bit 100 will typically be selected from a range of standard sizes (in mm) of 0.76, 1.0, 1.1, 1.5, 1.8, 2.0, 2.9, 3.2, 4.5 and 5.0, preferably from 2.5 and above, especially 3.2, 4.5 and 5.

In a typical drilling operation, the drill bit 100 is first rotated in a clockwise or right-handed direction when viewed from the rear of the shank 130 and urged towards the bone surface 10 to be drilled so that the apex 111 punctures the bone surface 10. As live bone is drilled, the swarf becomes a slurry of bone particles, blood and fat. The slurry flows up the flutes 140 which extend in an opposing left-handed direction as the bone is drilled. Upon removal of the drill bit 100 from the drill hole whilst still rotating the drill bit 100 in a clockwise direction, a wiping effect is created which essentially clears the slurry from the flutes 140 and deposits it back into the drill hole. This wiping effect is created by virtue of the orientation of the helix of the flutes 140 (that is, opposing the direction of rotation during the drilling operation). This is in contrast to a standard drill bit in which the swarf typically remains in the flutes as the drill bit is retracted out of the hole. Consequently, drilling with the drill bit 100 may diminish the need for the surgeon to manually reintroduce ejected bone swarf back into the hole or use other means of augmentation such as cement, synthetic bone, allografts and the like.

A drill bit 200 according to a second embodiment is depicted in FIGS. 6 through 10 of the accompanying drawings. Features of the drill bit 200 that are identical to those of the drill bit 100 are provided with an identical reference numeral, whereas equivalent features are provided with the same reference numeral to that of the first embodiment, increased by 100.

The drill bit 200 is of identical construction to the drill bit 100 of the first embodiment, apart from the configuration of the tip 210.

Figure 7:
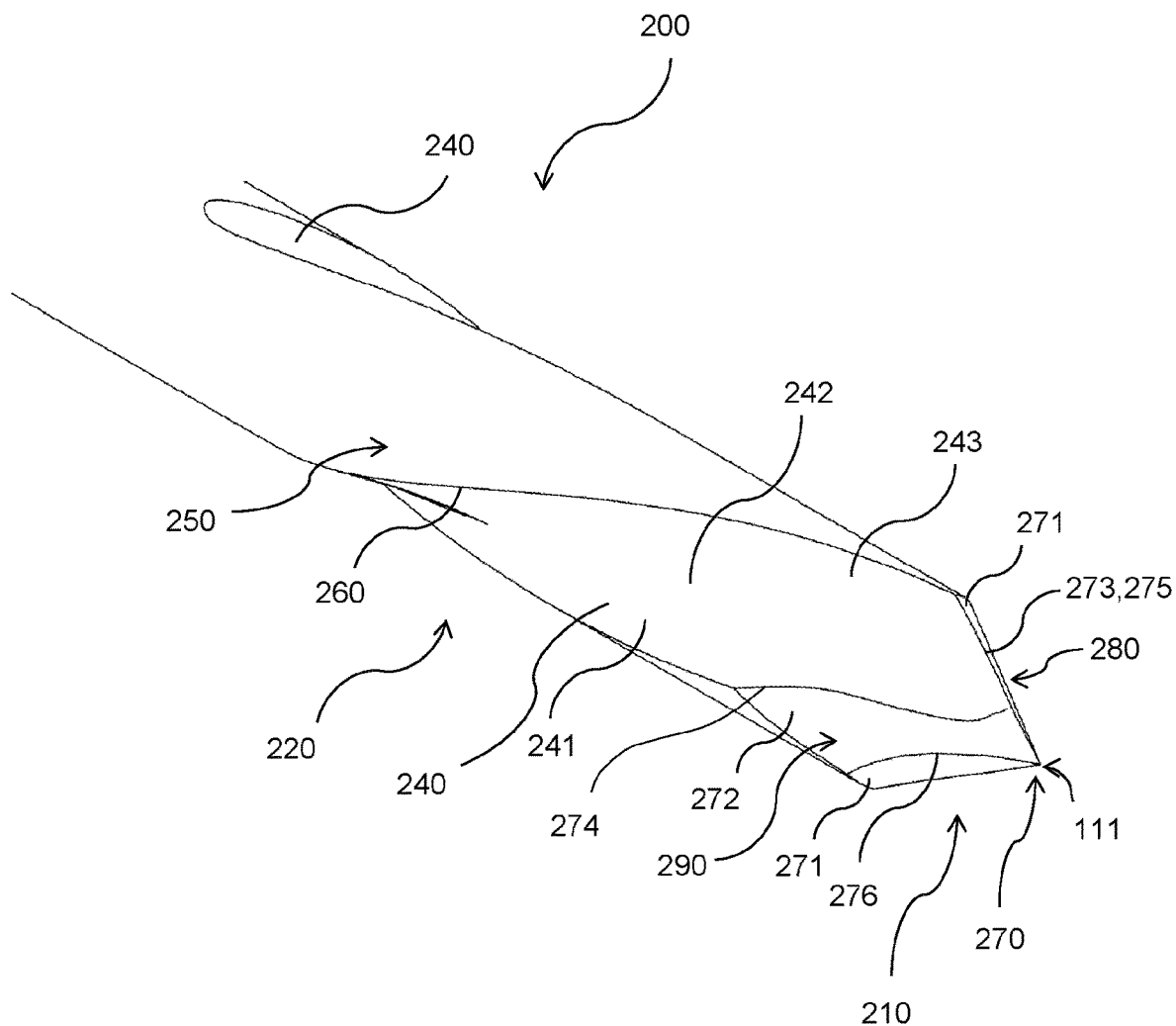
FIG. 7 is an enlarged perspective view of the tip of the drill bit of FIG. 6.
Figure 9:
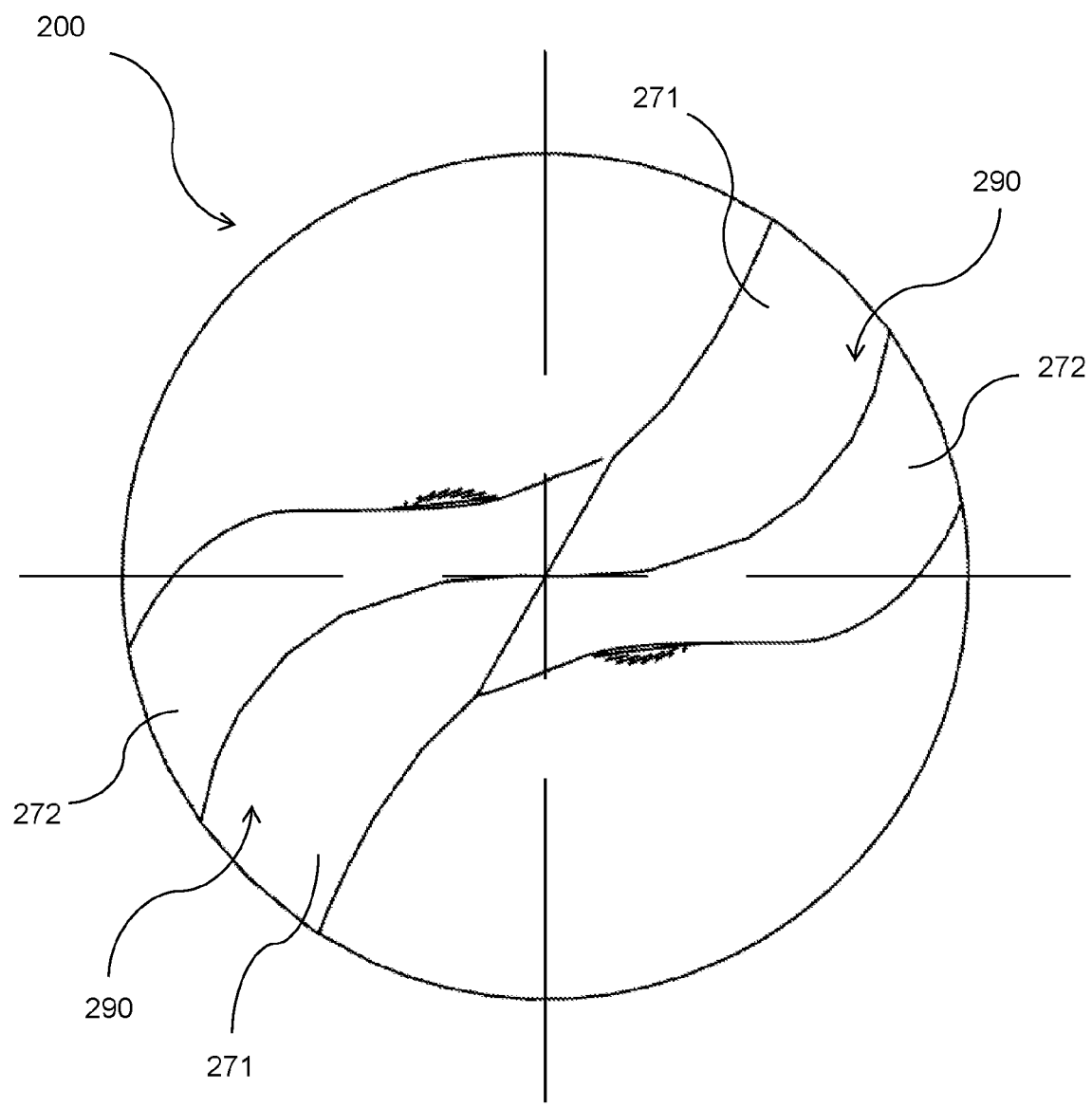
FIG. 9 is an enlarged end elevation view of the drill bit of FIG. 6.
Figure 11:
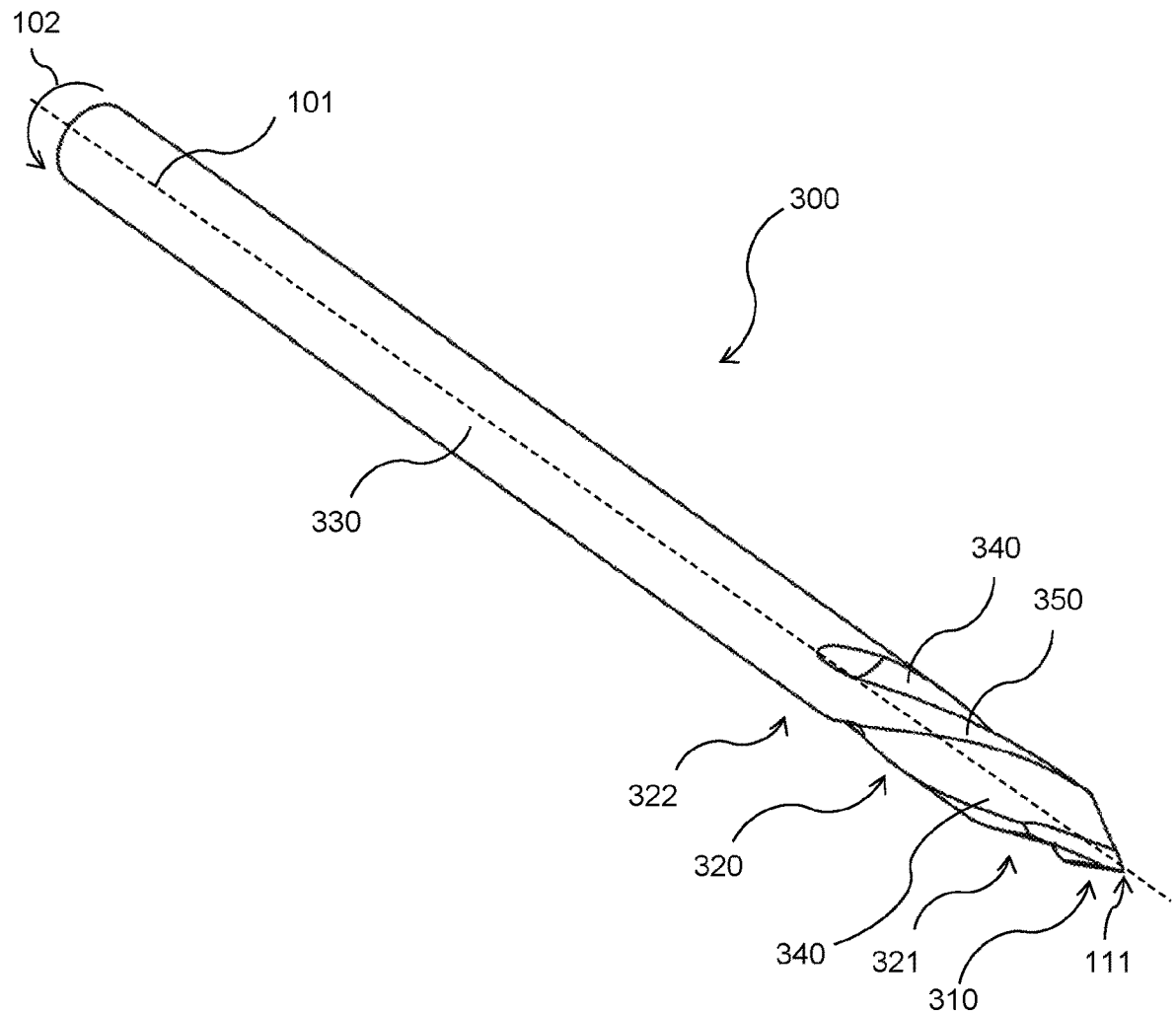
FIG. 11 is a perspective view of a drill bit according to a third embodiment of the invention.

In contrast to the first embodiment, each tip face 290 comprises a leading primary facet 271 and a trailing secondary facet 272 inclined relative to the primary facet 271 as best depicted in FIGS. 7 and 9. Each of the primary facets 271 has a tip face leading edge 273 and each of the secondary facets 272 has a tip face trailing edge 274. A tip face intermediate edge 276 is defined at the intersection of the primary facet 271 and the secondary facet 272.

Figure 8:
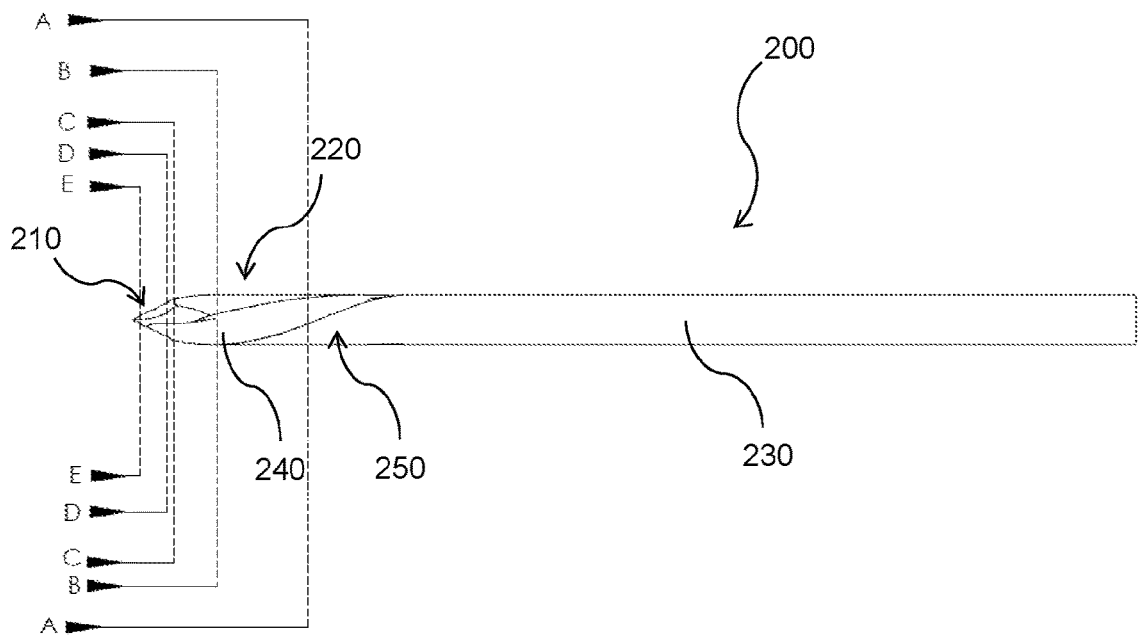
FIG. 8 is a first front elevation view of the drill bit of FIG. 6.
Figures 8A, 8B:
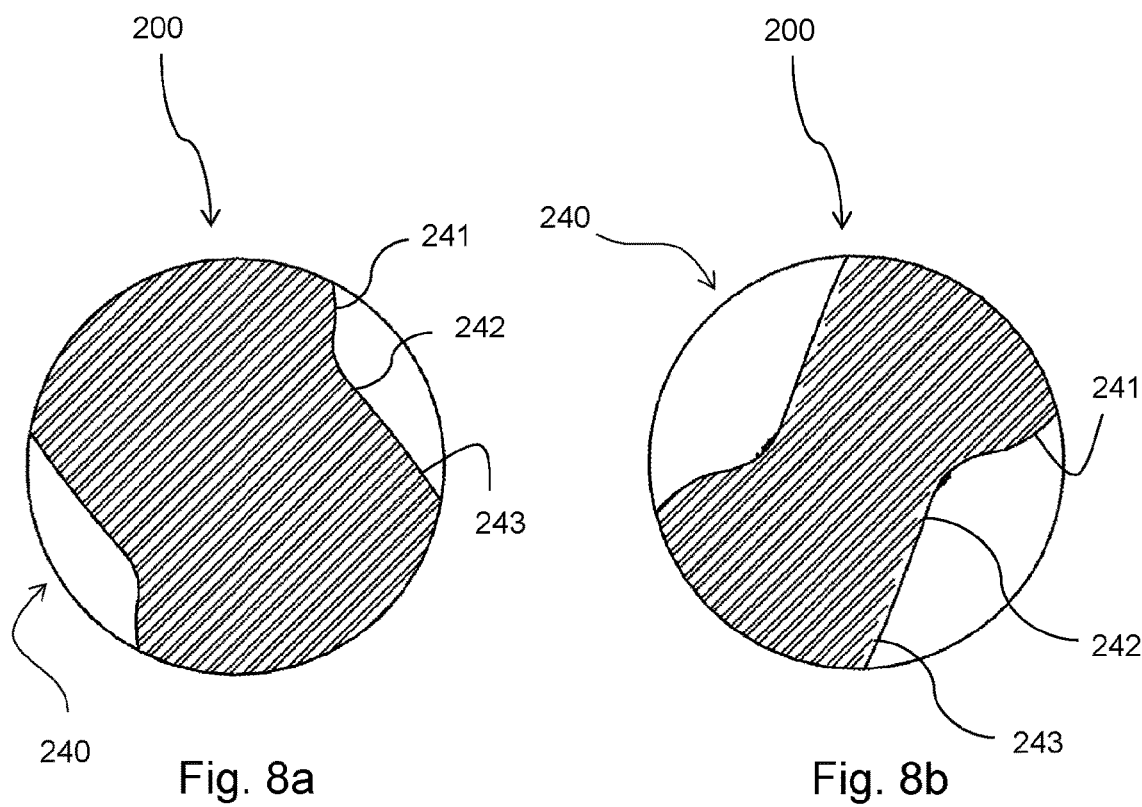
FIGS. 8a through 8e are each cross-sectional views of the drill bit of FIG. 6 taken at sections A-A to E-E of FIG. 8 respectively.
Figure 8C:
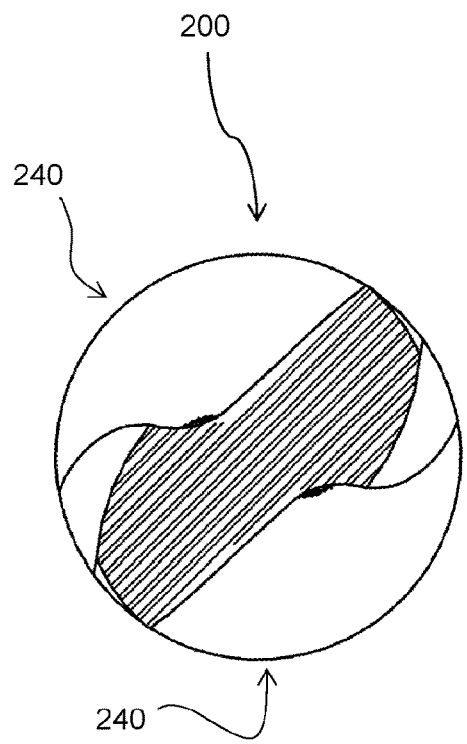
Figure 8D:
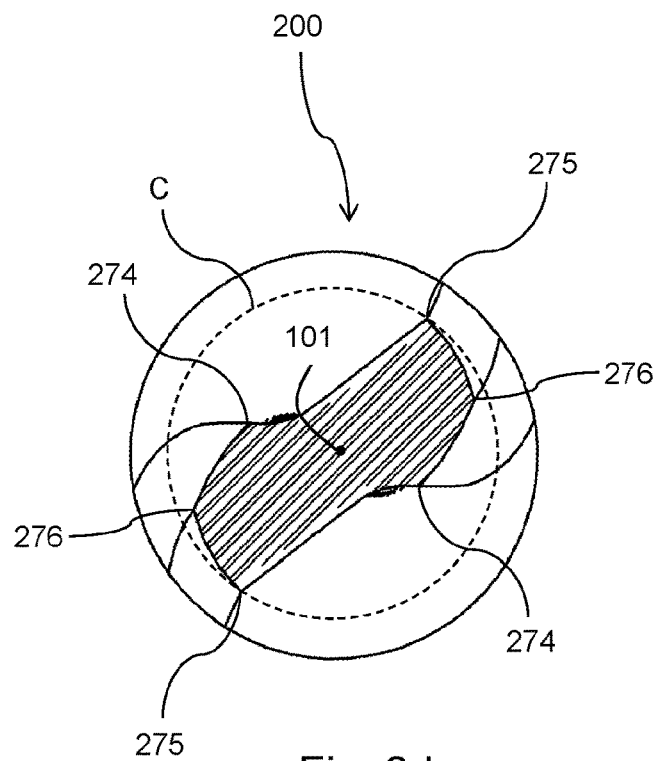

As best depicted in FIG. 7, each of the tip faces 290, at the tip face leading edge 273 of the primary facet 271, forms an intersection with an adjacent flute 240 to define a primary cutting edge 275. In substantially any tip cross-sectional plane extending perpendicular to the axis 101 through the primary cutting edges 275 (as best depicted in the cross-sectional view of FIG. 8d), each of the primary cutting edges 275 lies on the circle C extending about the axis 101 and each of the tip face trailing edges 274 and each of the tip face intermediate edges 276 lies entirely within the circle C.

As with the first embodiment, each of the tip faces 290 of the drill bit 200 has two regions, being a forward tip face region 270 and a rear tip face region 280 as best depicted in FIG. 7. Each forward tip face region 270 extends from adjacent the end of the flutes 240 to the apex 111 and constitutes the solid forward end of the tip 210. Each rear tip face region 280 constitutes the region extending from the forward tip face region 270 to the forward end of the adjacent body land 250. The rear tip face regions 280 are each separated by one of the flutes 240. Each of the primary facets 271 and each of the secondary facets 272 extend along the rear tip face region 280 and the forward tip face region 270 to the apex 111.

Figure 8E:
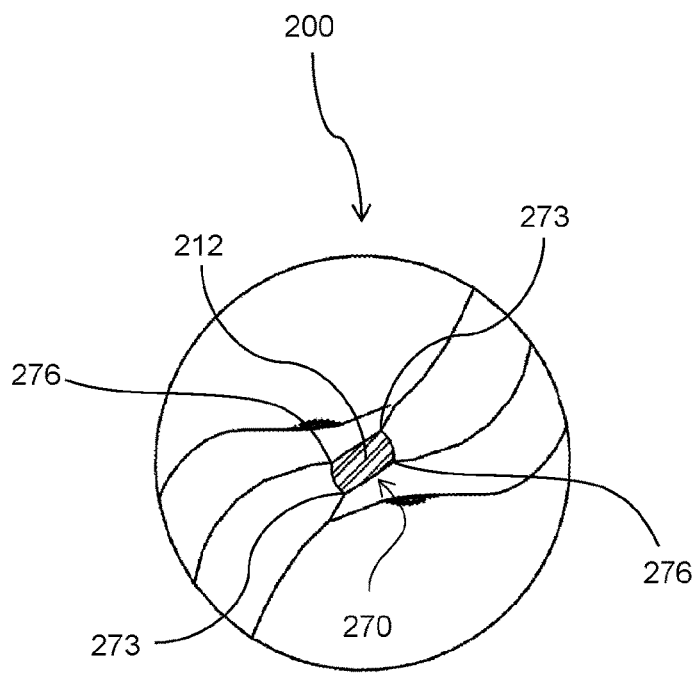

As with the first embodiment, the forward tip face region 270 defines a substantially diamond-shaped pyramid of the forward extremity of the tip 210 where each of the opposing pyramidal edges of the pyramid form included angles. As best depicted in the cross-sectional view of FIG. 8e, this approximately translates to a parallelogram 212 in cross-section where one diagonal of the parallelogram 212 is greater than the other. Those corners of the parallelogram 212 which are located on the longer diagonal of the parallelogram 212 lie on one of the respective tip face leading edges 273 in the forward tip face region 270. Those corners of the parallelogram 212 which are located on the shorter diagonal lie on one of the respective tip face intermediate edges 276 in the forward tip face region 270. The intersection of each of the pyramidal edges of the pyramid defines a sharp point at the apex 111 as best depicted in FIG. 7.

Each of the primary facets 271 and each of the secondary facets 272 are concavely curved about the axis 101 towards the drilling direction 102 to assist the flow of bone swarf along the flutes 240 towards the rear of the drill bit 200 during a drilling operation.

It will be appreciated that the drill bit 200 according to the second embodiment operates in substantially the same manner as the drill bit 100 according to the first embodiment.

A drill bit 300 according to a third embodiment is depicted in FIGS. 11 through 15 of the accompanying drawings. Features of the drill bit 300 that are identical to those of the drill bit 100 are provided with an identical reference numeral, whereas equivalent features are provided with the same reference numeral to that of the first embodiment, increased by 200.

The drill bit 300 is of similar basic construction to the drill bit 100 of the first embodiment, apart from the number of the flutes 340 and the configuration of the tip 310.

Figure 13:
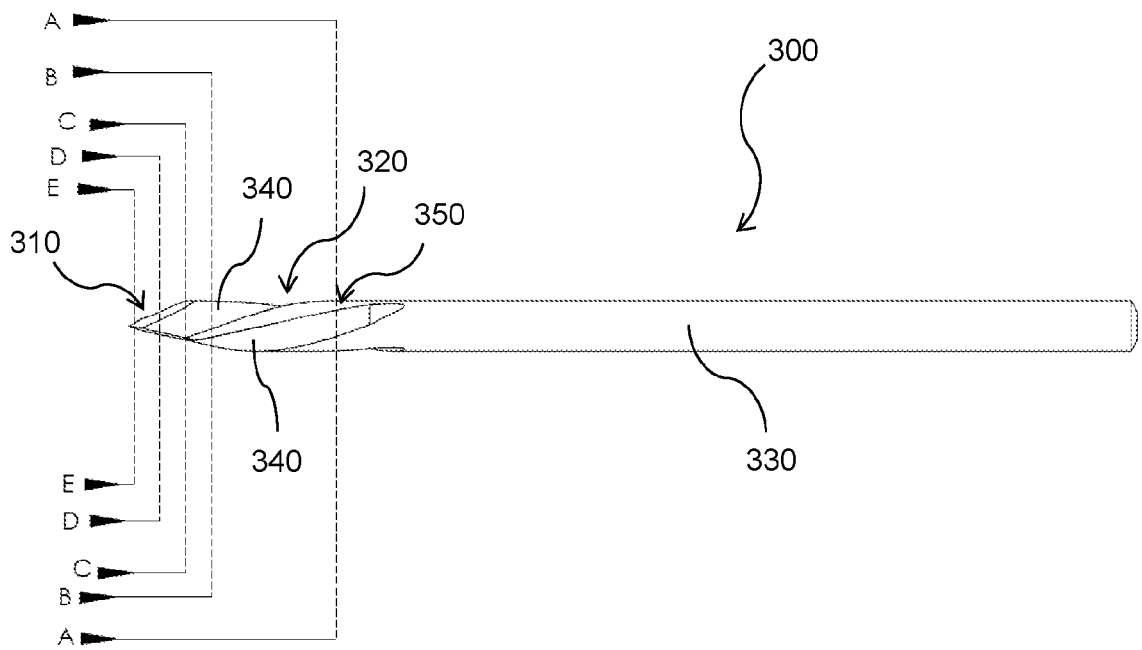
FIG. 13 is a first front elevation view of the drill bit of FIG. 11.
Figure 13A:
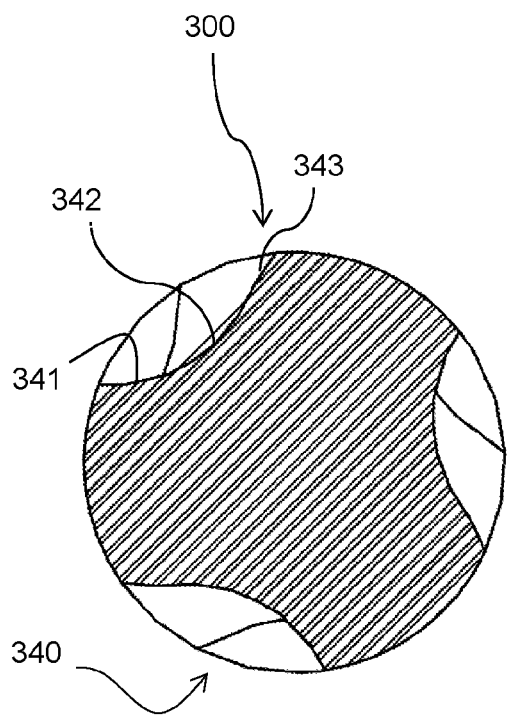
FIGS. 13a through 13e are each cross-sectional views of the drill bit of FIG. 11 taken at sections A-A to E-E of FIG. 13 respectively.
Figure 13B:
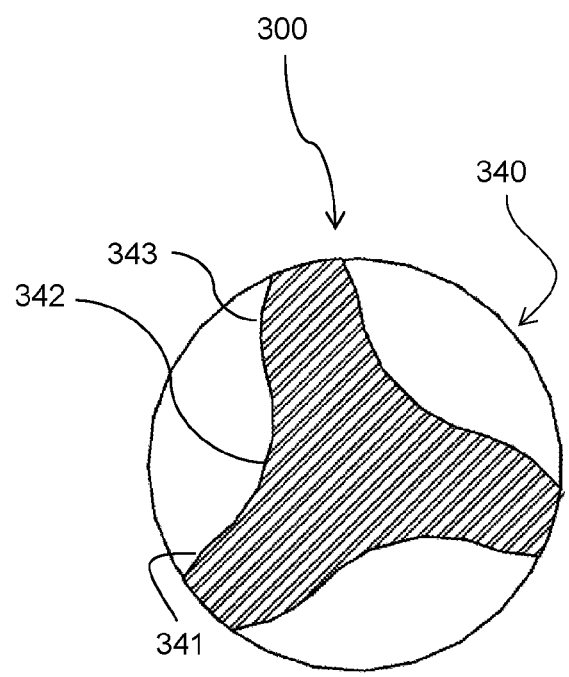
Figure 13C:
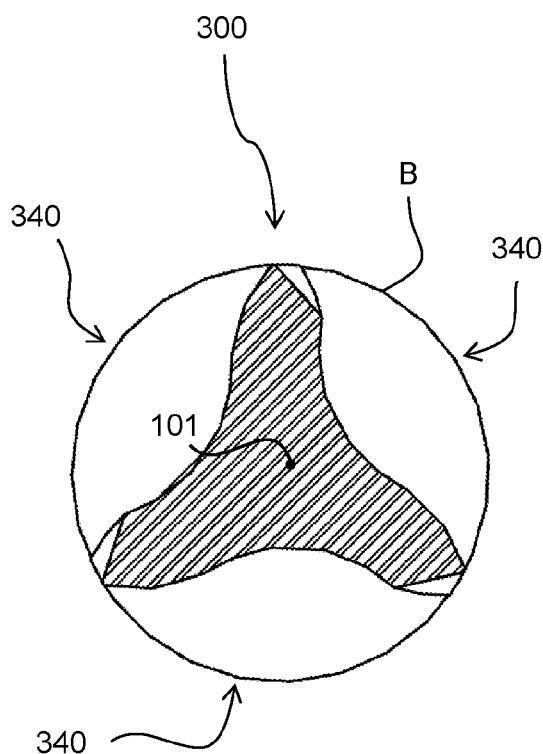

In contrast with the first embodiment, there are three flutes 340 formed in the drill bit 300. As best depicted in the cross-sectional view of FIG. 13c, each of the flutes 340 subtends an arc of typically about 100 to 110 degrees measured on the circle B extending about the axis 101.

Figure 12:
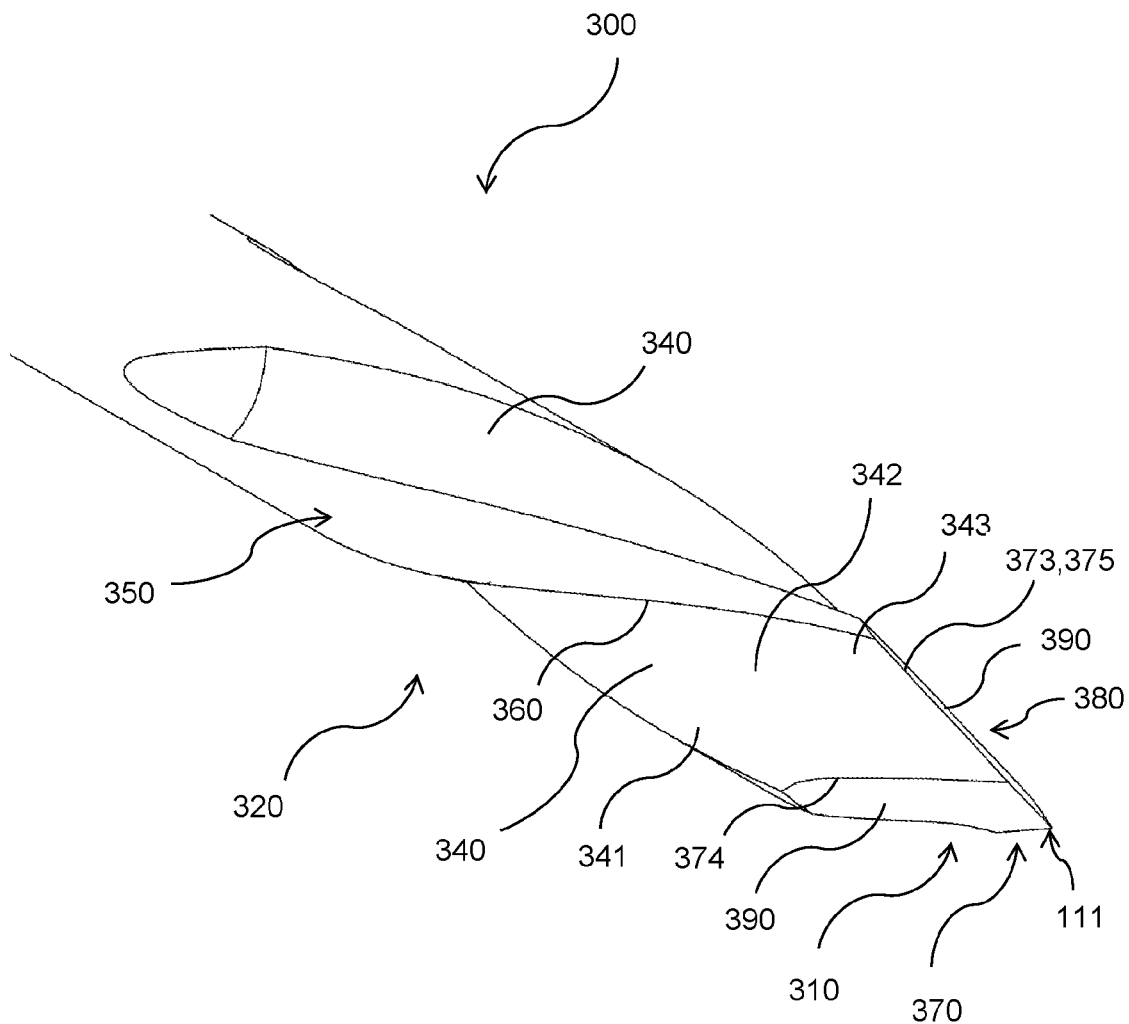
FIG. 12 is an enlarged perspective view of the tip of the drill bit of FIG. 11.
Figure 13D:
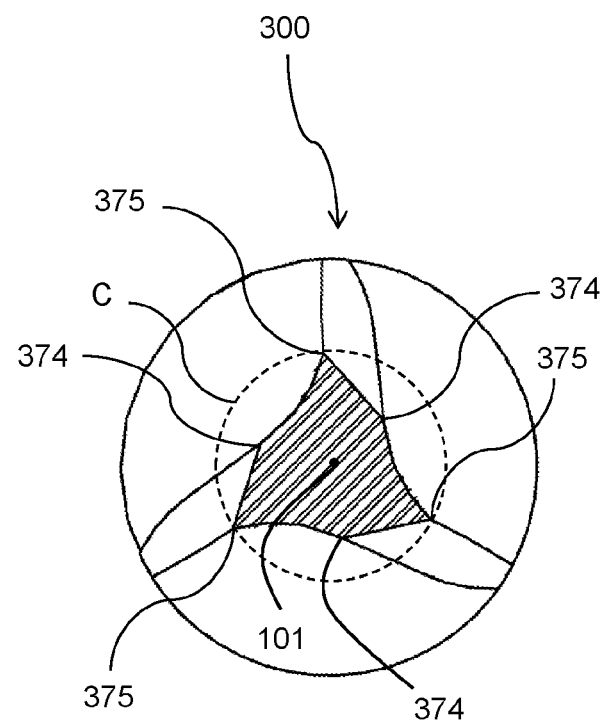
Figure 14:
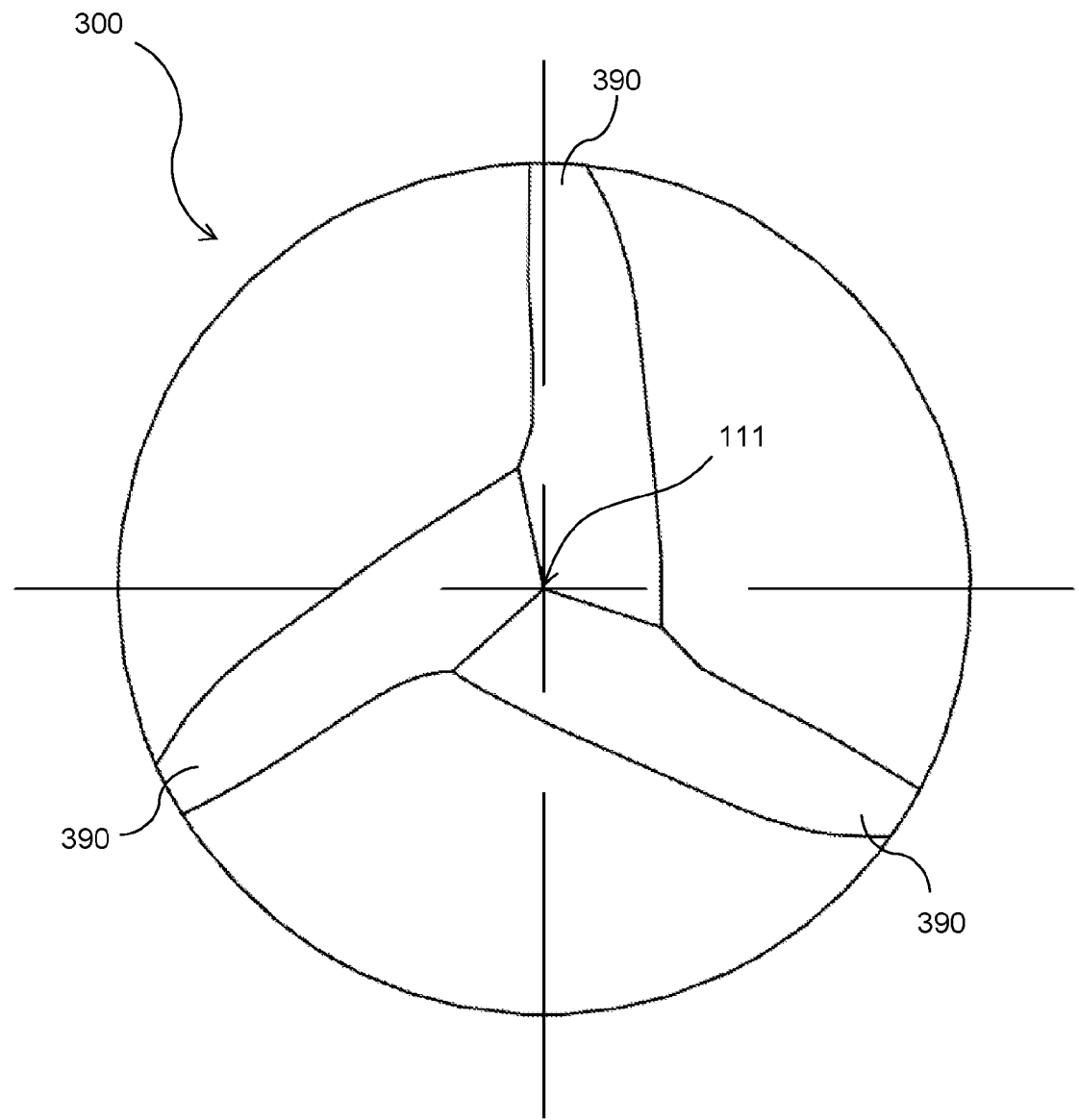
FIG. 14 is an enlarged end elevation view of the drill bit of FIG. 11.
Figure 16:
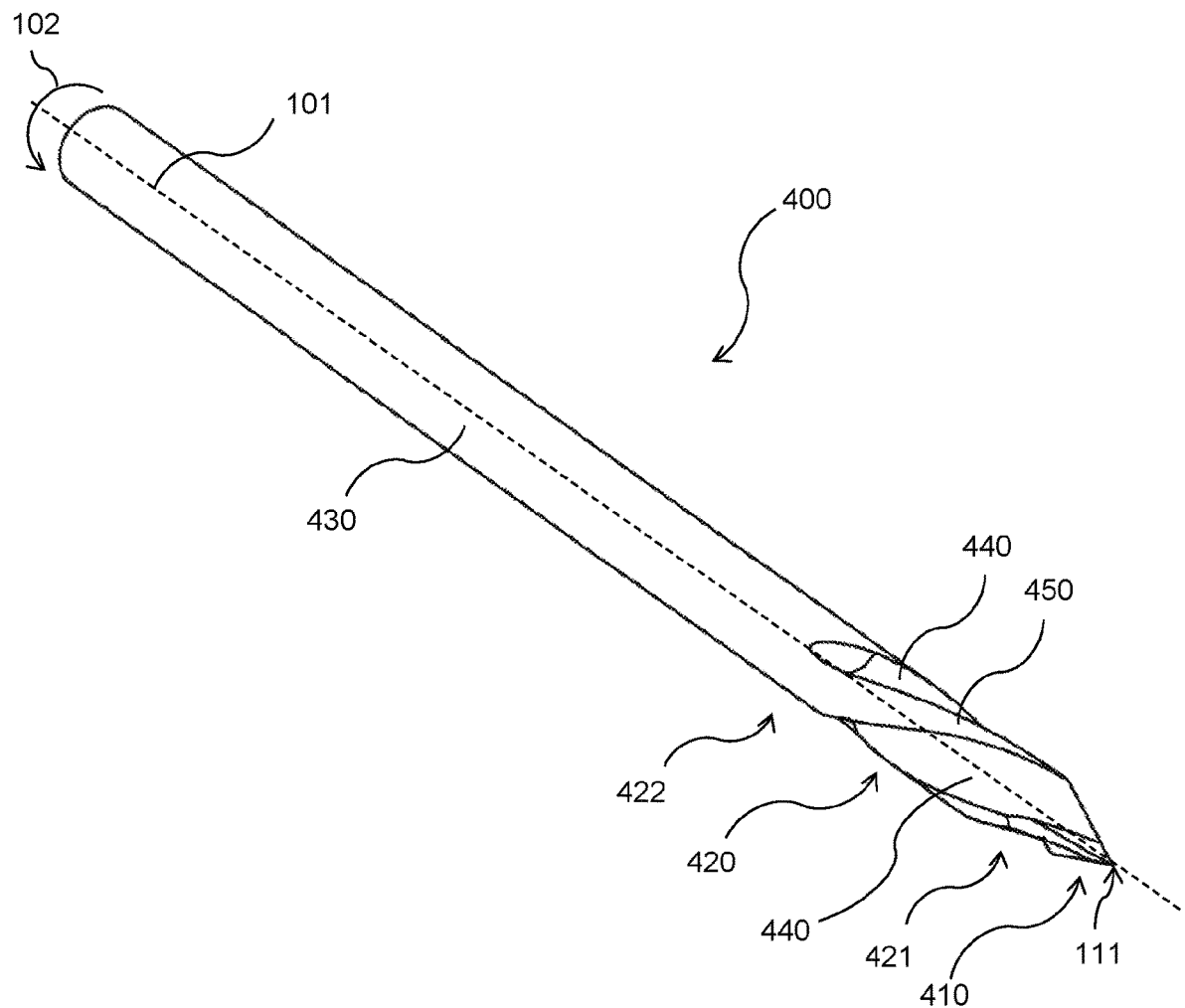
FIG. 16 is a perspective view of a drill bit according to a fourth embodiment of the invention.

In contrast with the first embodiment, three tip faces 390 are defined on the tip 310 and each extend from a corresponding body land 350 to the apex 111 as best depicted in FIGS. 12 and 14. As with the first embodiment, each of the tip faces 390 has a tip face leading edge 373 and a tip face trailing edge 374. Each of the tip faces 390, at the tip face leading edge 373, forms an intersection with an adjacent flute 340 to define a primary cutting edge 375. In substantially any tip cross-sectional plane extending perpendicular to the axis 101 through the primary cutting edges 375 (as best depicted in the cross-sectional view of FIG. 13d), each of the primary cutting edges 375 lies on the circle C extending about the axis 101 and each of the tip face trailing edges 374 lies entirely within the circle C.

As with the first embodiment, each of the tip faces 390 of the drill bit 300 has two regions, being a forward tip face region 370 and a rear tip face region 380 as best depicted in FIG. 12. Each forward tip face region 370 extends from adjacent the end of the flutes 340 to the apex 111 and constitutes the solid forward end of the tip 310. Each rear tip face region 380 constitutes the region extending from the forward tip face region 370 to the forward end of the adjacent body land 350. The rear tip face regions 380 are each separated by one of the flutes 340.

Figure 13E:
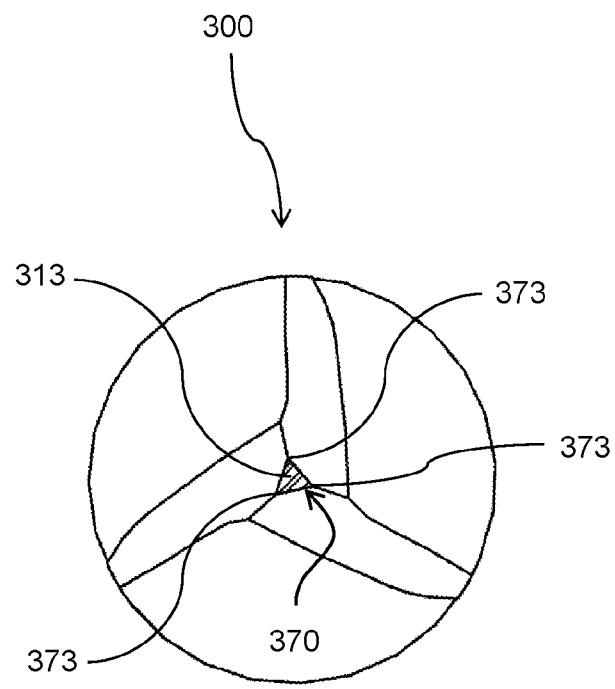

In contrast with the first embodiment, the forward tip face region 370 defines a substantially triangle-shaped pyramid of the forward extremity of the tip 310. As best depicted in the cross-sectional view of FIG. 13e, this approximately translates to a triangle 313 in cross-section where each of the vertices of the triangle 313 lie on one of the respective tip face leading edges 373 in the forward tip face region 370. The intersection of each of the pyramidal edges of the pyramid defines a sharp point at the apex 111 as best depicted in FIG. 12.

It will be appreciated that the drill bit 300 according to the third embodiment operates in substantially the same manner as the drill bit 100 according to the first embodiment.

A drill bit 400 according to a fourth embodiment is depicted in FIGS. 16 through 20 of the accompanying drawings. Features of the drill bit 400 that are identical to those of the drill bit 300 are provided with an identical reference numeral, whereas equivalent features are provided with the same reference numeral to that of the third embodiment, increased by 100.

The drill bit 400 is of identical construction to the drill bit 300 of the third embodiment, apart from the configuration of the tip 410.

Figure 17:
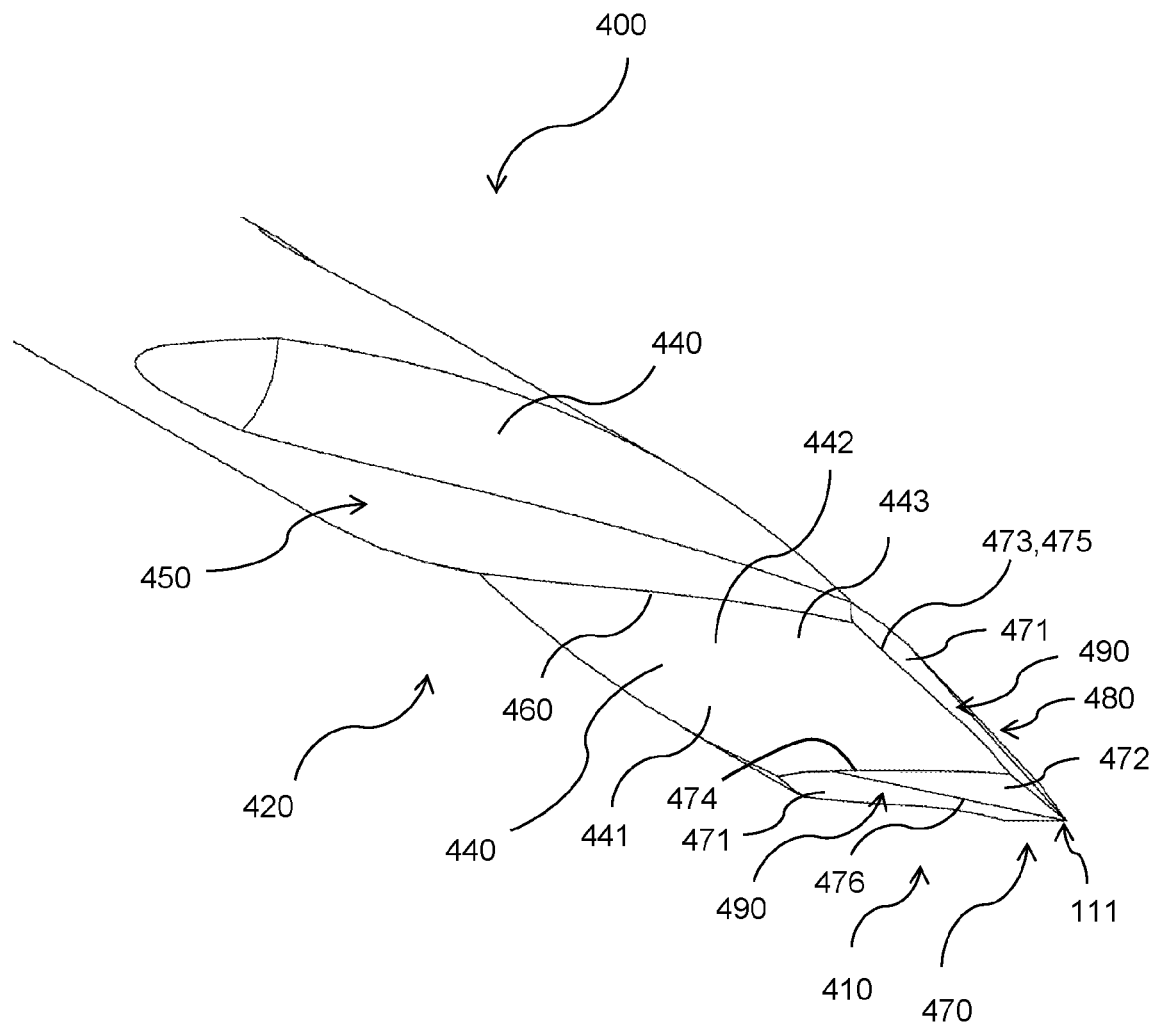
FIG. 17 is an enlarged perspective view of the tip of the drill bit of FIG. 16.
Figure 19:
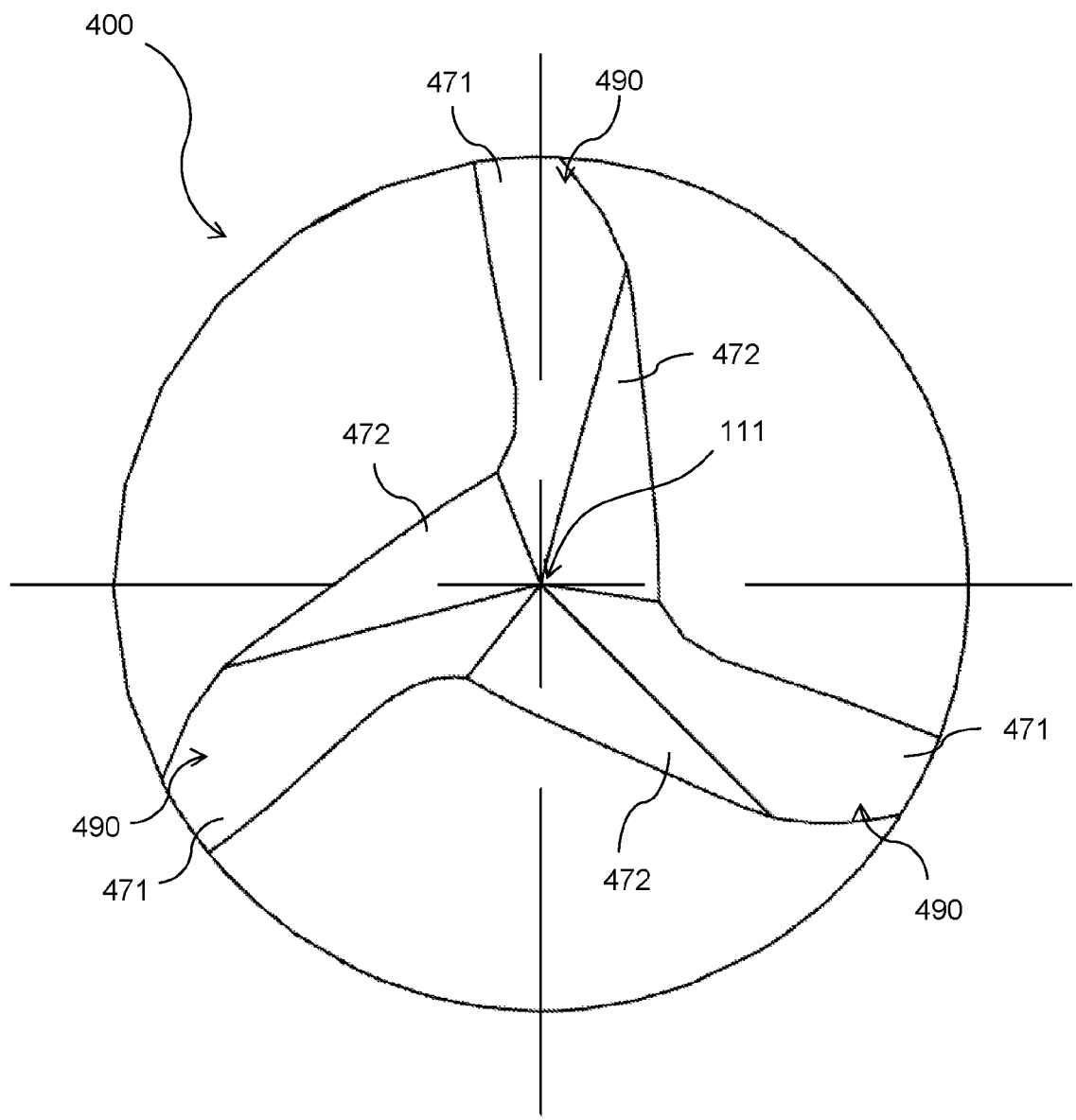
FIG. 19 is an enlarged end elevation view of the drill bit of FIG. 16.
Figure 20:
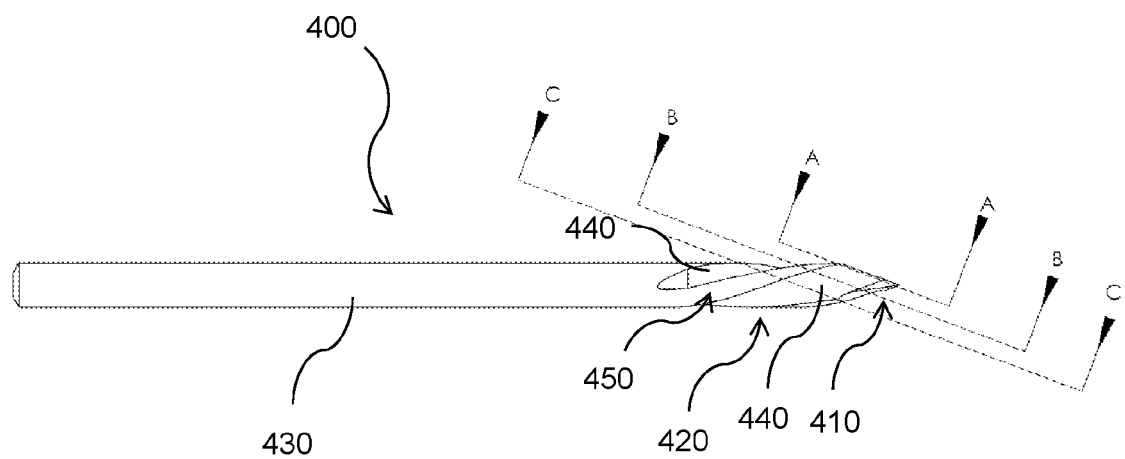
FIG. 20 is a second front elevation view of the drill bit of FIG. 16.
Figure 20A:
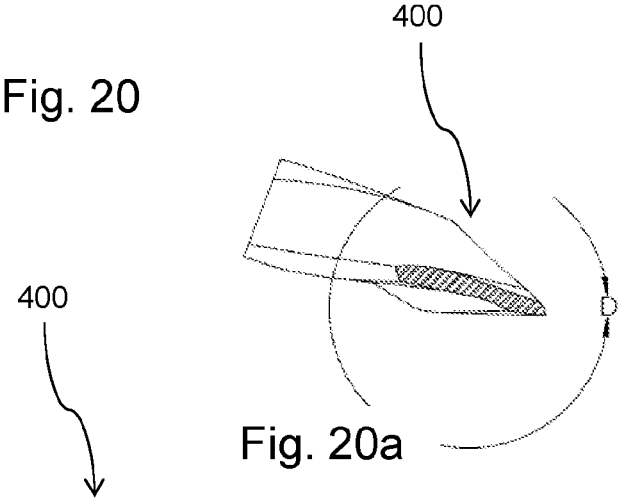
FIGS. 20a through 20c are each perspective/fragmentary cross-sectional views of the drill bit of FIG. 16 taken at sections A-A to C-C of FIG. 20 respectively.
Figure 20B:
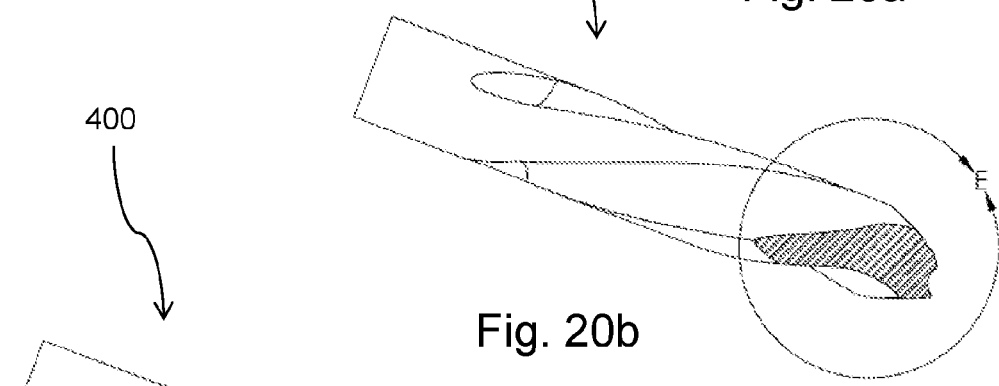
Figure 20C:
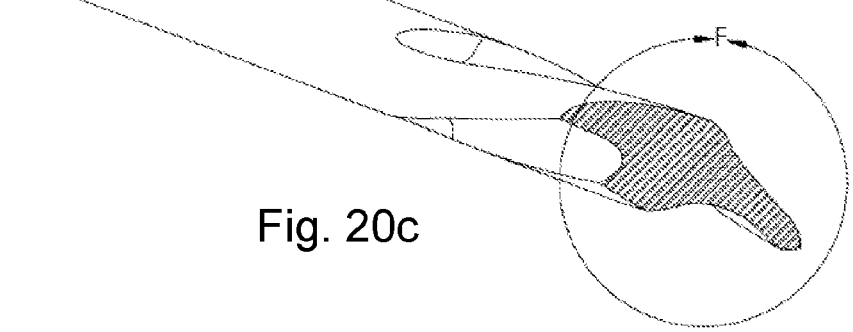
Figure 21:
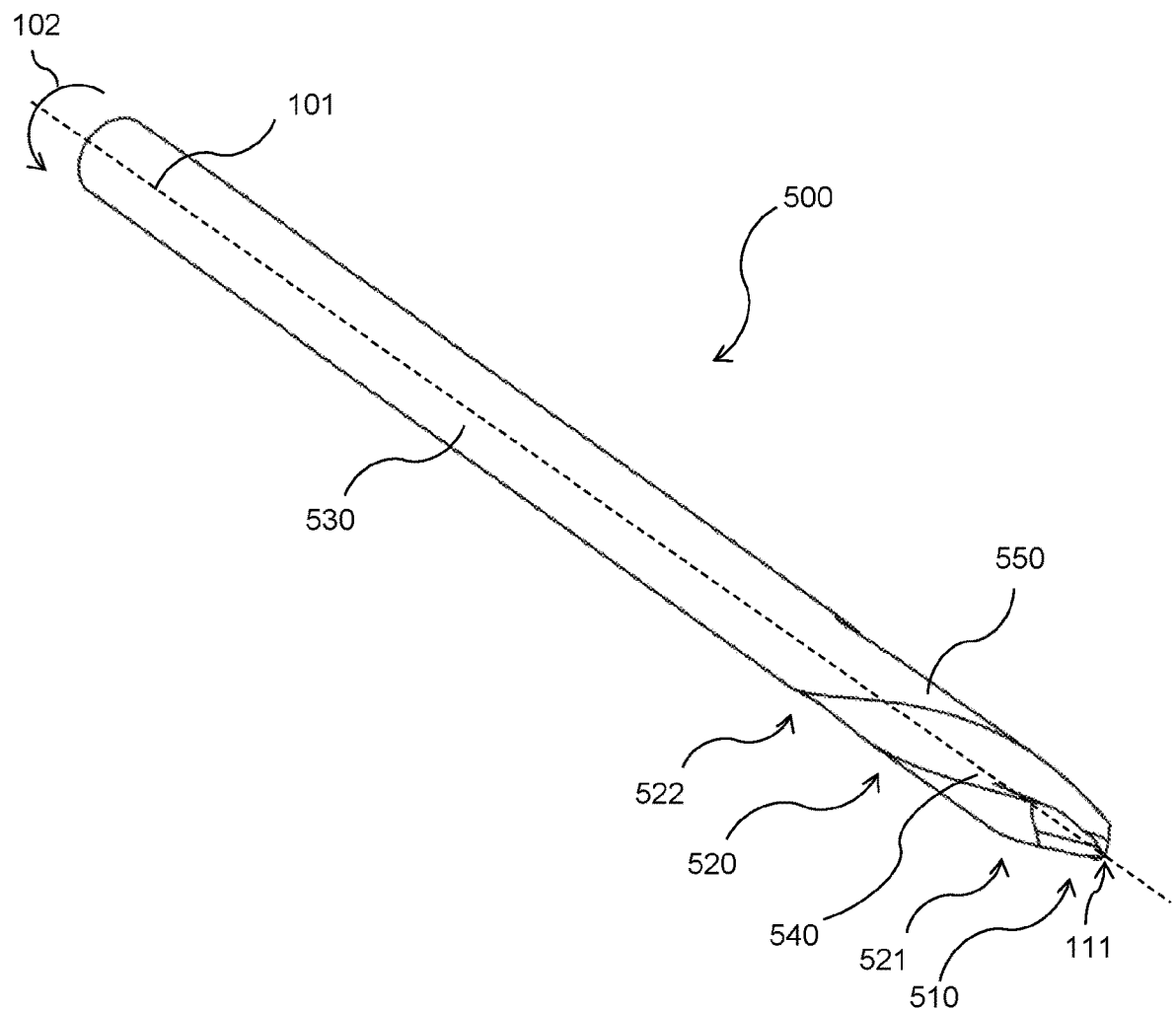
FIG. 21 is a perspective view of a drill bit according to a fifth embodiment of the invention.

In contrast to the third embodiment, each tip face 490 comprises a leading primary facet 471 and a trailing secondary facet 472 inclined relative to the primary facet 471 as best depicted in FIGS. 17 and 19. Each of the secondary facets 472 may form the basis of a relief section. A tip face leading edge 473 is defined by the leading edge of the primary facet 471. A tip face trailing edge 474 is defined by both the trailing edge of the primary facet 471 and the trailing edge of the secondary facet 472. A tip face intermediate edge 476 is defined at the intersection of the primary facet 471 and the secondary facet 472.

Figure 18:
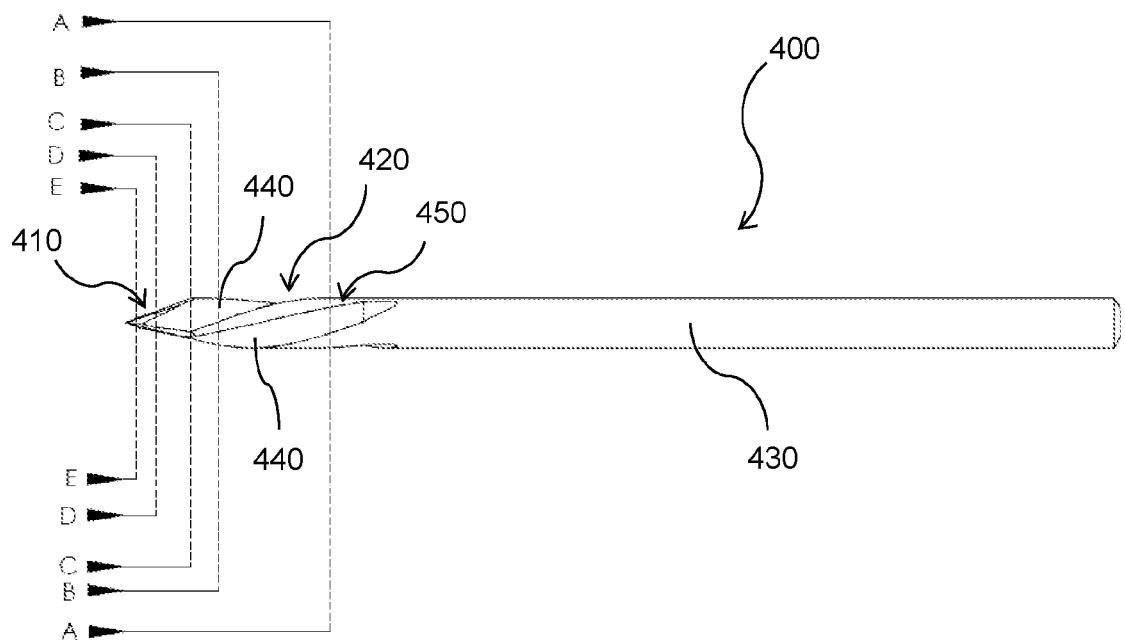
FIG. 18 is a first front elevation view of the drill bit of FIG. 16.
Figure 18A:
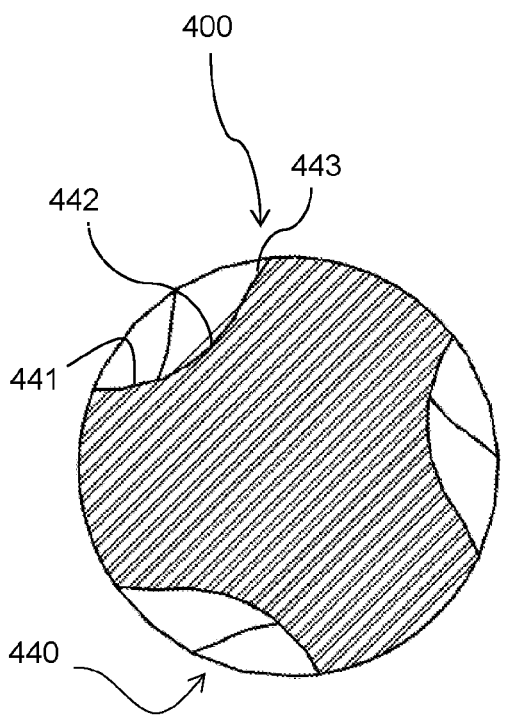
FIGS. 18a through 18e are each cross-sectional views of the drill bit of FIG. 16 taken at sections A-A to E-E of FIG. 18 respectively.
Figure 18B:
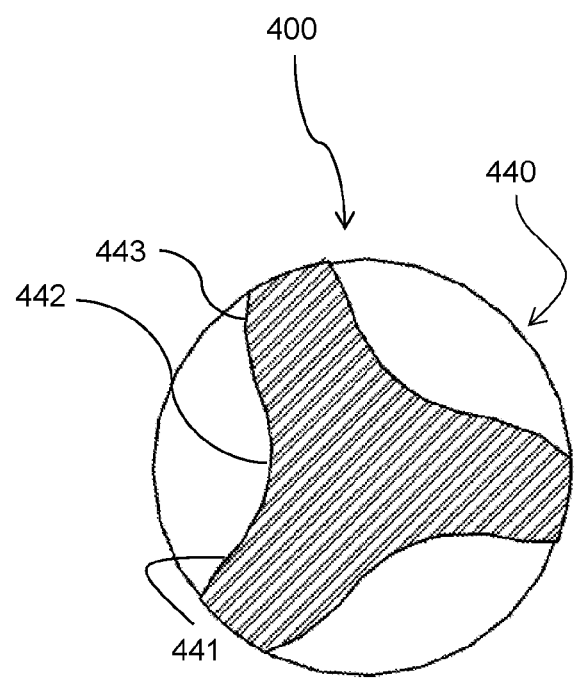
Figure 18C:
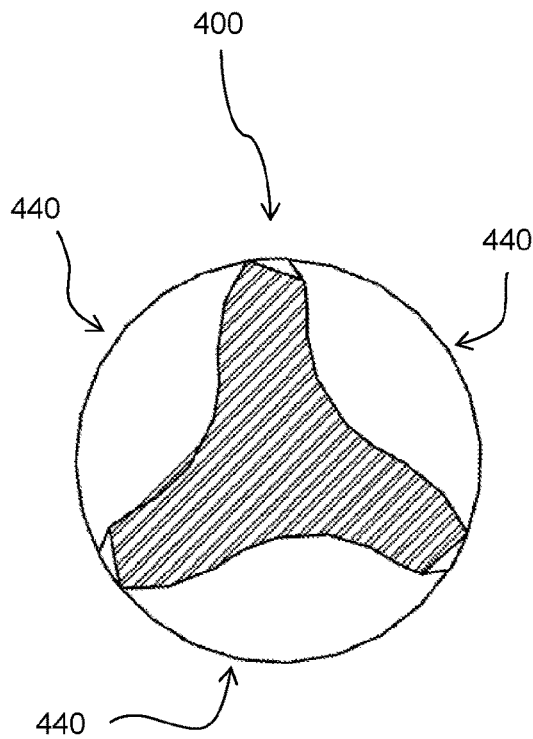
Figure 18D:
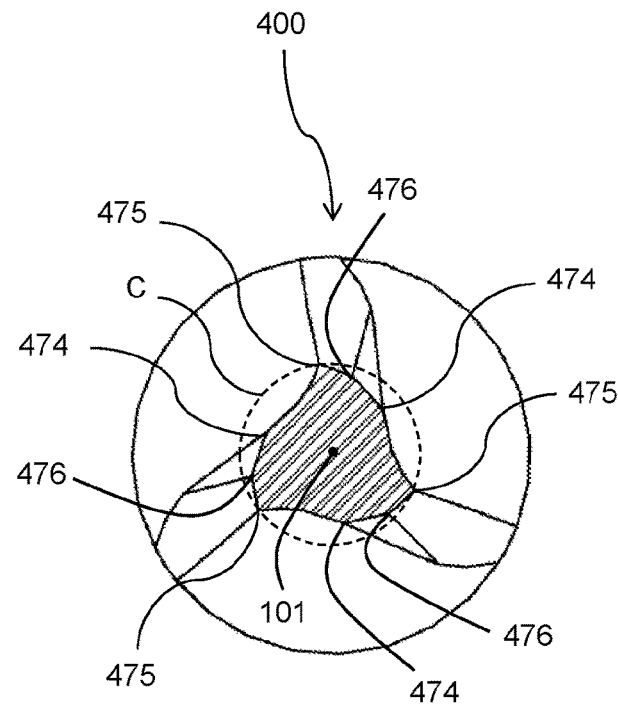

Each of the tip faces 490, at the tip face leading edge 473 of the primary facet 471, forms an intersection with an adjacent flute 440 to define a primary cutting edge 475. In substantially any tip cross-sectional plane extending perpendicular to the axis 101 through the primary cutting edges 475 (as best depicted in the cross-sectional view of FIG. 18d), each of the primary cutting edges 475 lies on the circle C extending about the axis 101 and each of the tip face trailing edges 474 and each of the tip face intermediate edges 476 lies entirely within the circle C.

As with the third embodiment, each of the tip faces 490 of the drill bit 400 has two regions, being a forward tip face region 470 and a rear tip face region 480 as best depicted in FIG. 17. Each forward tip face region 470 extends from adjacent the end of the flutes 440 to the apex 111 and constitutes the solid forward end of the tip 410. Each rear tip face region 480 constitutes the region extending from the forward tip face region 470 to the forward end of the adjacent body land 450. The rear tip face regions 480 are each separated by one of the flutes 440. Each of the primary facets 471 and each of the secondary facets 472 extend along the rear tip face region 480 and the forward tip face region 470 to the apex 111.

Figure 18E:
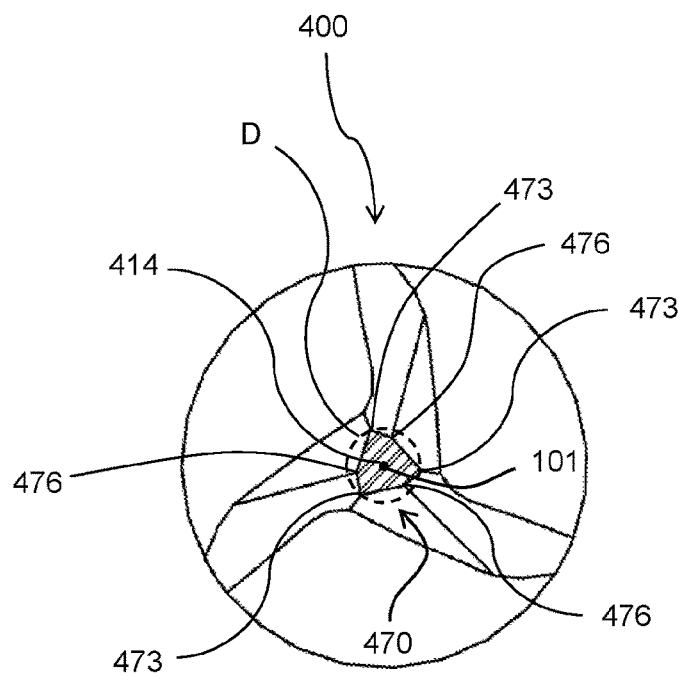

In contrast with the third embodiment, the forward tip face region 470 defines an irregular hexagonal-shaped pyramid of the forward extremity of the tip 410 where each of the opposing pyramidal edges of the pyramid form included angles. As best depicted in the cross-sectional view of FIG. 18e, this approximately translates to an irregular hexagon 414 in cross-section. Those corners of the irregular hexagon 414 which are located on a circle D extending about the axis 101 lie on one of the respective tip face leading edges 473 in the forward tip face region 470. Those corners of the irregular hexagon 414 which are located entirely within the circle D lie on one of the respective tip face intermediate edges 476 in the forward tip face region 470. The intersection of each of the pyramidal edges of the pyramid defines a sharp point at the apex 111 as best depicted in FIG. 17.

It will be appreciated that the drill bit 400 according to the fourth embodiment operates in substantially the same manner as the drill bit 300 according to the third embodiment.

A drill bit 500 according to a fifth embodiment is depicted in FIGS. 21 through 25 of the accompanying drawings. Features of the drill bit 500 that are identical to those of the drill bit 200 are provided with an identical reference numeral, whereas equivalent features are provided with the same reference numeral to that of the second embodiment, increased by 300.

The drill bit 500 is of similar basic construction to the drill bit 200 of the second embodiment, apart from the configuration of the tip 510.

Figure 22:
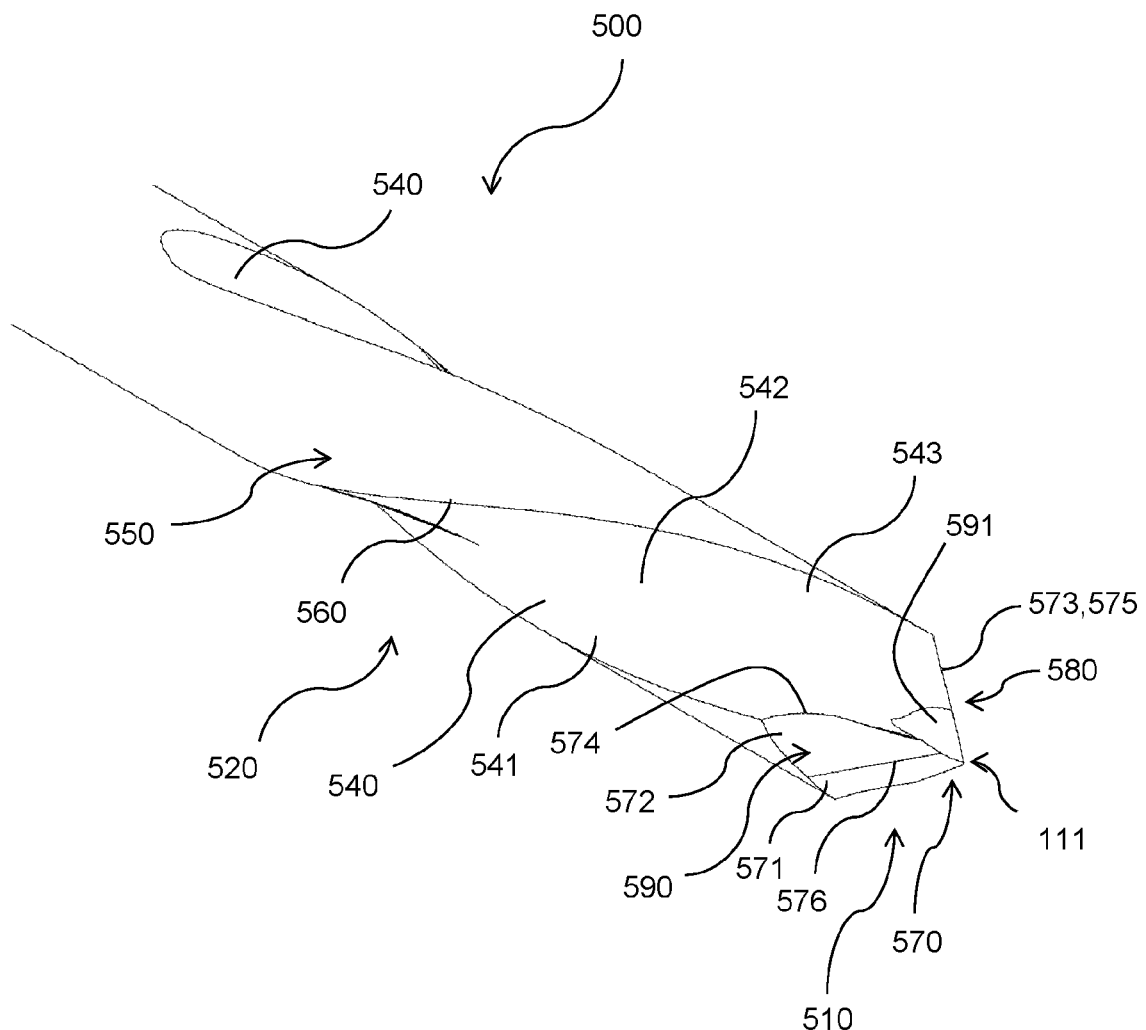
FIG. 22 is an enlarged perspective view of the tip of the drill bit of FIG. 21.
Figure 24:
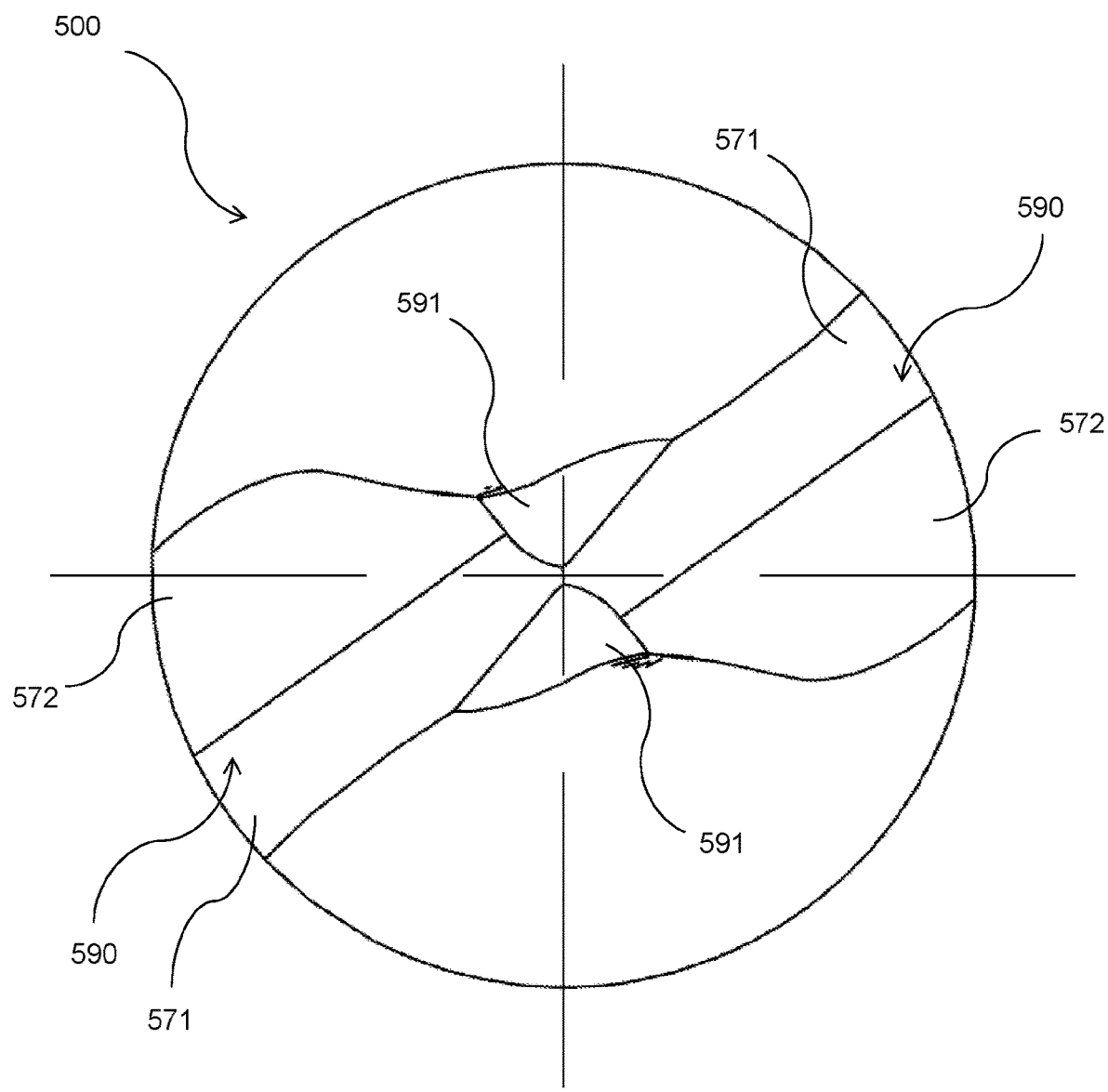
FIG. 24 is an enlarged end elevation view of the drill bit of FIG. 21.
Figure 25:
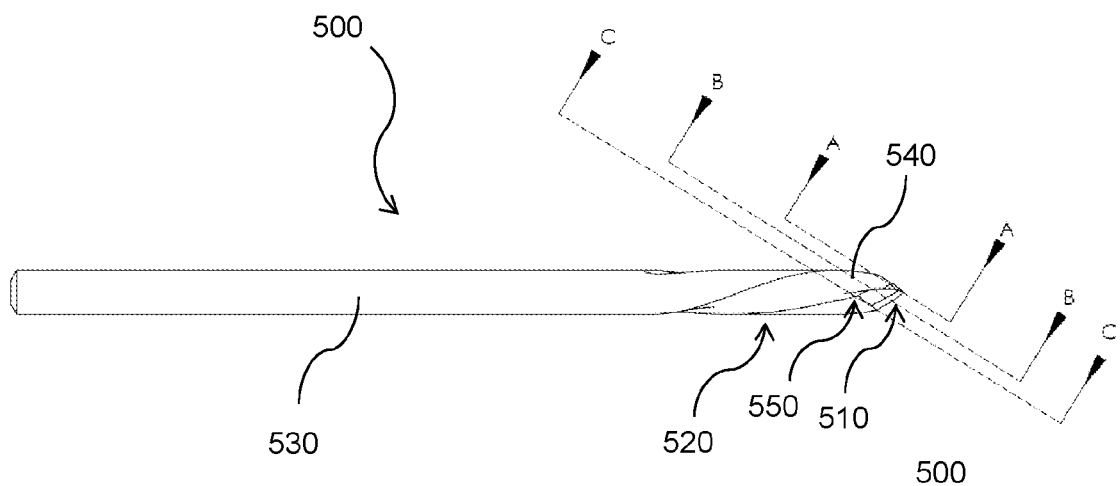
FIG. 25 is a second front elevation view of the drill bit of FIG. 21.
Figure 25A:
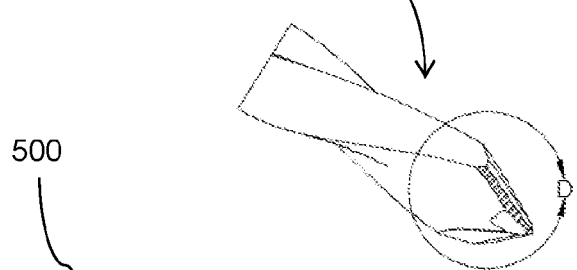
FIGS. 25a through 25c are each perspective/fragmentary cross-sectional views of the drill bit of FIG. 21 taken at sections A-A to C-C of FIG. 25 respectively.
Figure 25B:
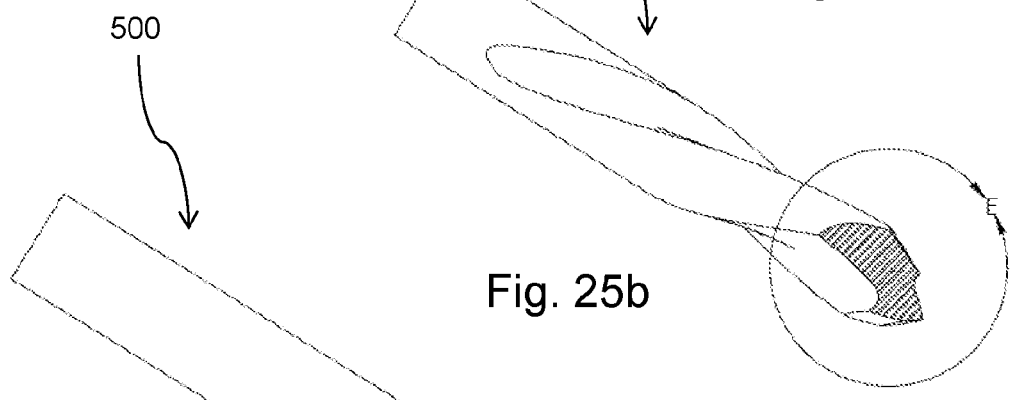
Figure 25C:
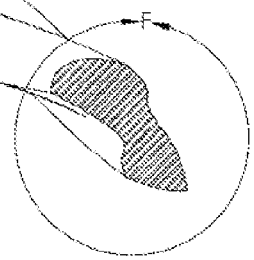
Figure 26:
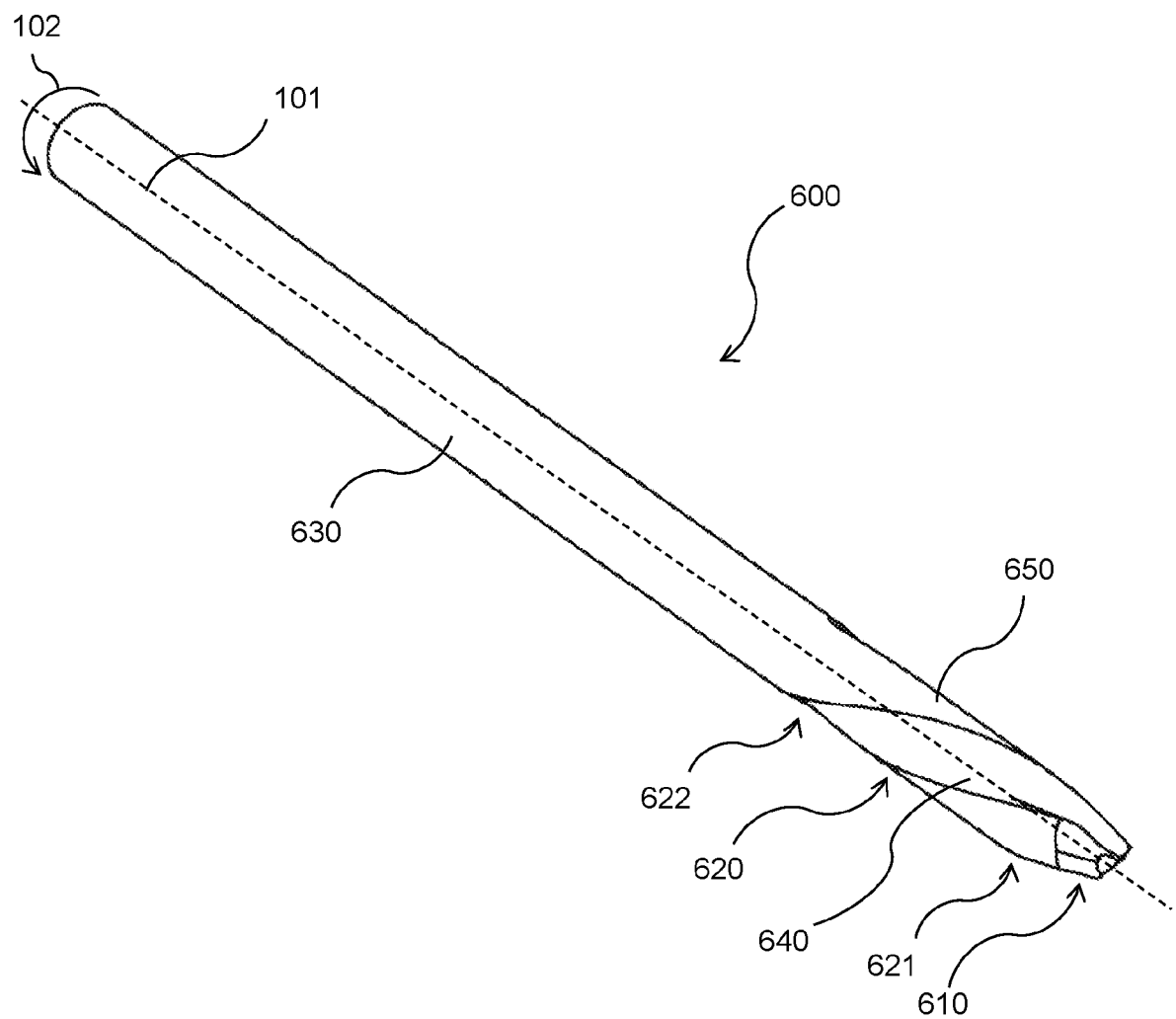
FIG. 26 is a perspective view of a drill bit according to a sixth embodiment of the invention.

As with the second embodiment, each tip face 590 comprises a leading primary facet 571 and a trailing secondary facet 572 inclined relative to the primary facet 571 as best depicted in FIGS. 22 and 24. Each of the primary facets 571 has a tip face leading edge 573 and each of the secondary facets 572 has a tip face trailing edge 574. A tip face intermediate edge 576 is defined at the intersection of the primary facet 571 and the secondary facet 572.

Figure 23:
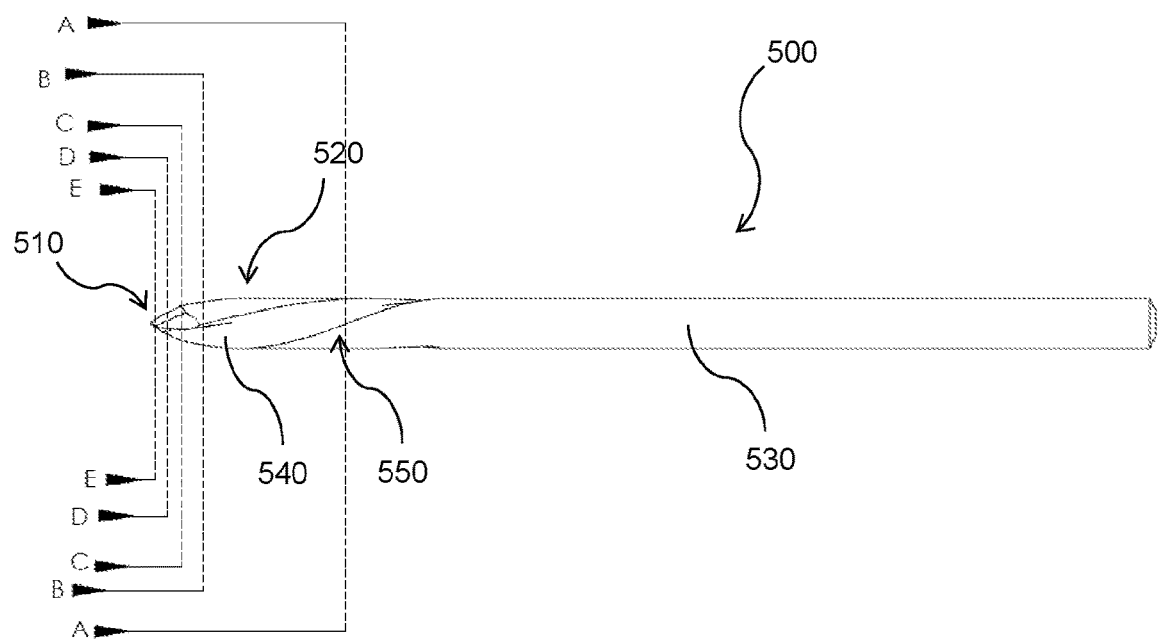
FIG. 23 is a first front elevation view of the drill bit of FIG. 21.
Figures 23A, 23B:
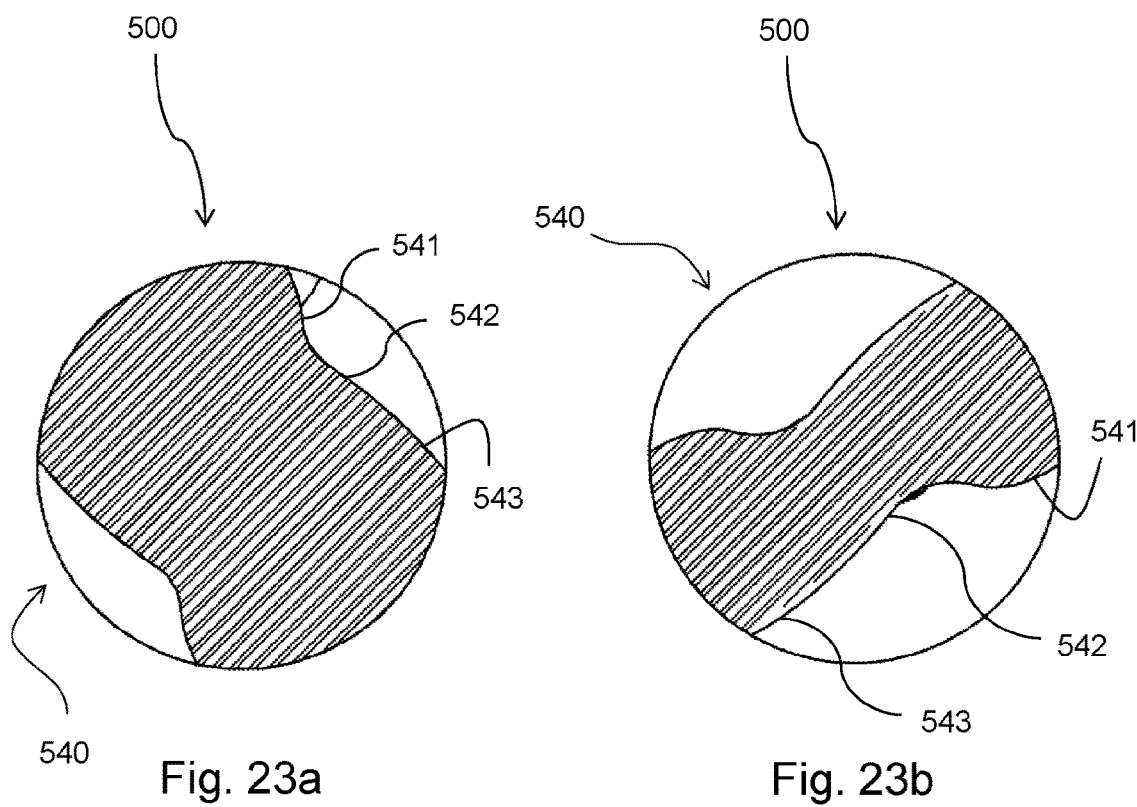
FIGS. 23a through 23e are each cross-sectional views of the drill bit of FIG. 21 taken at sections A-A to E-E of FIG. 23 respectively.
Figure 23C:
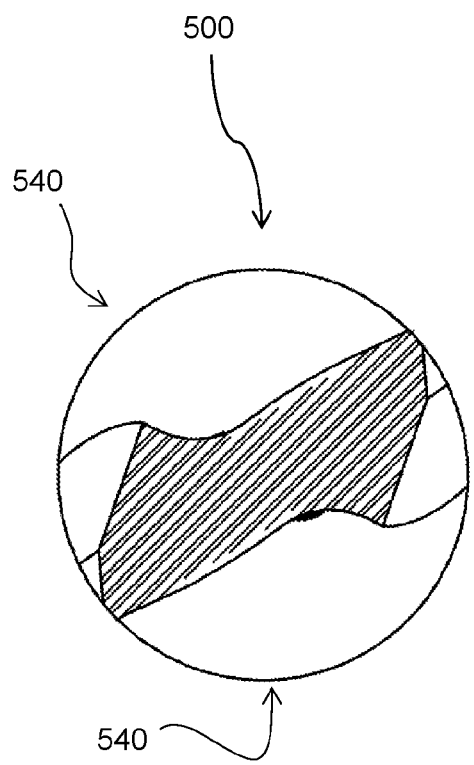
Figure 23D:
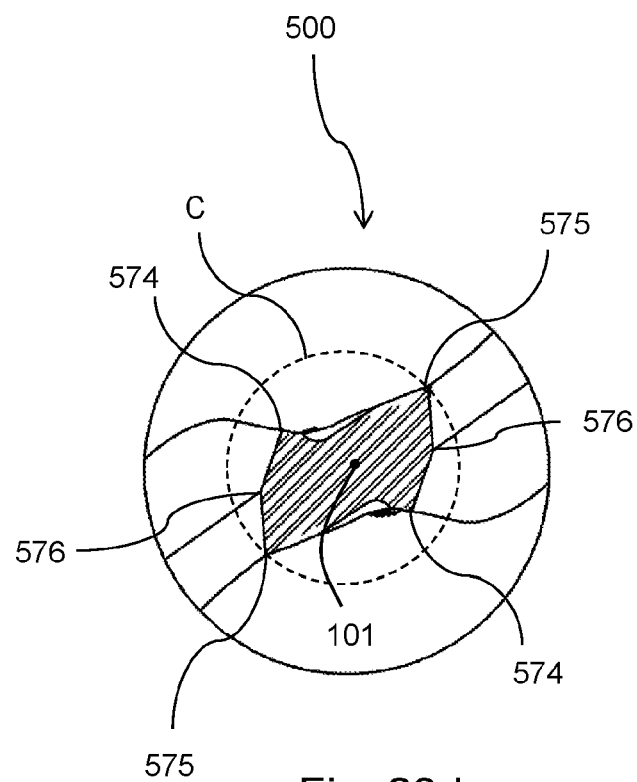

Each of the tip faces 590, at the tip face leading edge 573 of the primary facet 571, forms an intersection with an adjacent flute 540 to define a primary cutting edge 575. In substantially any tip cross-sectional plane extending perpendicular to the axis 101 through the primary cutting edges 575 (as best depicted in the cross-sectional view of FIG. 23*d*), each of the primary cutting edges 575 lies on the circle C extending about the axis 101 and each of the tip face trailing edges 574 and each of the tip face intermediate edges 576 lies entirely within the circle C.

As with the second embodiment, each of the tip faces 590 of the drill bit 500 has two regions, being a forward tip face region 570 and a rear tip face region 580 as best depicted in FIG. 22. Each forward tip face region 570 extends from adjacent the end of the flutes 540 to the apex 111 and constitutes the solid forward end of the tip 510. Each rear tip face region 580 constitutes the region extending from the forward tip face region 570 to the forward end of the adjacent body land 550. The rear tip face regions 580 are each separated by one of the flutes 540. Each of the primary facets 571 and each of the secondary facets 572 extend along the rear tip face region 580 and the forward tip face region 570 to the apex 111.

Figure 23E:
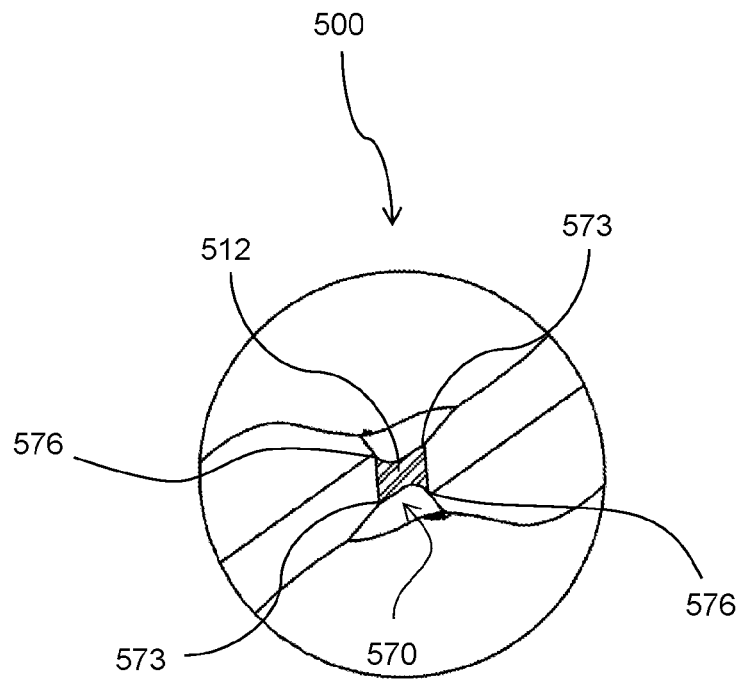

In contrast to the second embodiment, each tip face 590 comprises a chamfer 591 part located in the forward tip face region 570. Without each of these chamfers 591, each of the tip faces 590 would inevitably define a chisel edge resulting from the configuration of their two planar faces. In a standard drill bit, the technique of chamfering the tip faces in the manner depicted may be referred to as a split point operation. These chamfered portions of the tip 510 may form the basis of an additional relief section. In this regard, the forward tip face region 570 defines a substantially diamond-shaped pyramid of the forward extremity of the tip 510 where each of the opposing pyramidal edges of the pyramid form included angles. As best depicted in the cross-sectional view of FIG. 23*e*, this approximately translates to a parallelogram 512 with a pair of opposing concave sides in cross-section where one diagonal of the parallelogram 512 is greater than the other. As with the second embodiment, those corners of the parallelogram 512 which are located on the longer diagonal of the parallelogram 512 lie on one of the respective tip face leading edges 573 in the forward tip face region 570. Those corners of the parallelogram 512 which are located on the shorter diagonal lie on one of the respective tip face intermediate edges 576 in the forward tip face region 570. The intersection of each of the pyramidal edges of the pyramid defines a sharp point at the apex 111 as best depicted in FIG. 22.

It will be appreciated that the drill bit 500 according to the fifth embodiment operates in substantially the same manner as the drill bit 200 according to the second embodiment. Additionally, the drill bit 500 would be more suited to higher load bone drilling applications, such as the lower limb bones in healthy patients, where increased bone thickness and density will require a stronger and potentially more aggressive drill point.

A drill bit 600 according to a sixth embodiment is depicted in FIGS. 26 through 30 of the accompanying drawings. Features of the drill bit 600 that are identical to those of the drill bit 500 are provided with an identical reference numeral, whereas equivalent features are provided with the same reference numeral to that of the fifth embodiment, increased by 100.

The drill bit 600 is of similar basic construction to the drill bit 500 of the fifth embodiment.

In contrast to the fifth embodiment, the drill bit 600 comprises a hole 605 extending longitudinally about the axis 101 from one end of the drill bit 600 to the other end of the drill bit 600. The diameter of the hole 605 is about 0.7 to 2.1 mm, typically about 1.1 mm. A guide wire of smaller diameter is inserted through the hole 605 to facilitate correct positioning of the drill bit 600 at the bone surface 10 where the intended drill hole is to be located. In this regard, the drill bit 600 passes along the guide wire following the intended trajectory towards the bone surface 10.

Figure 27:
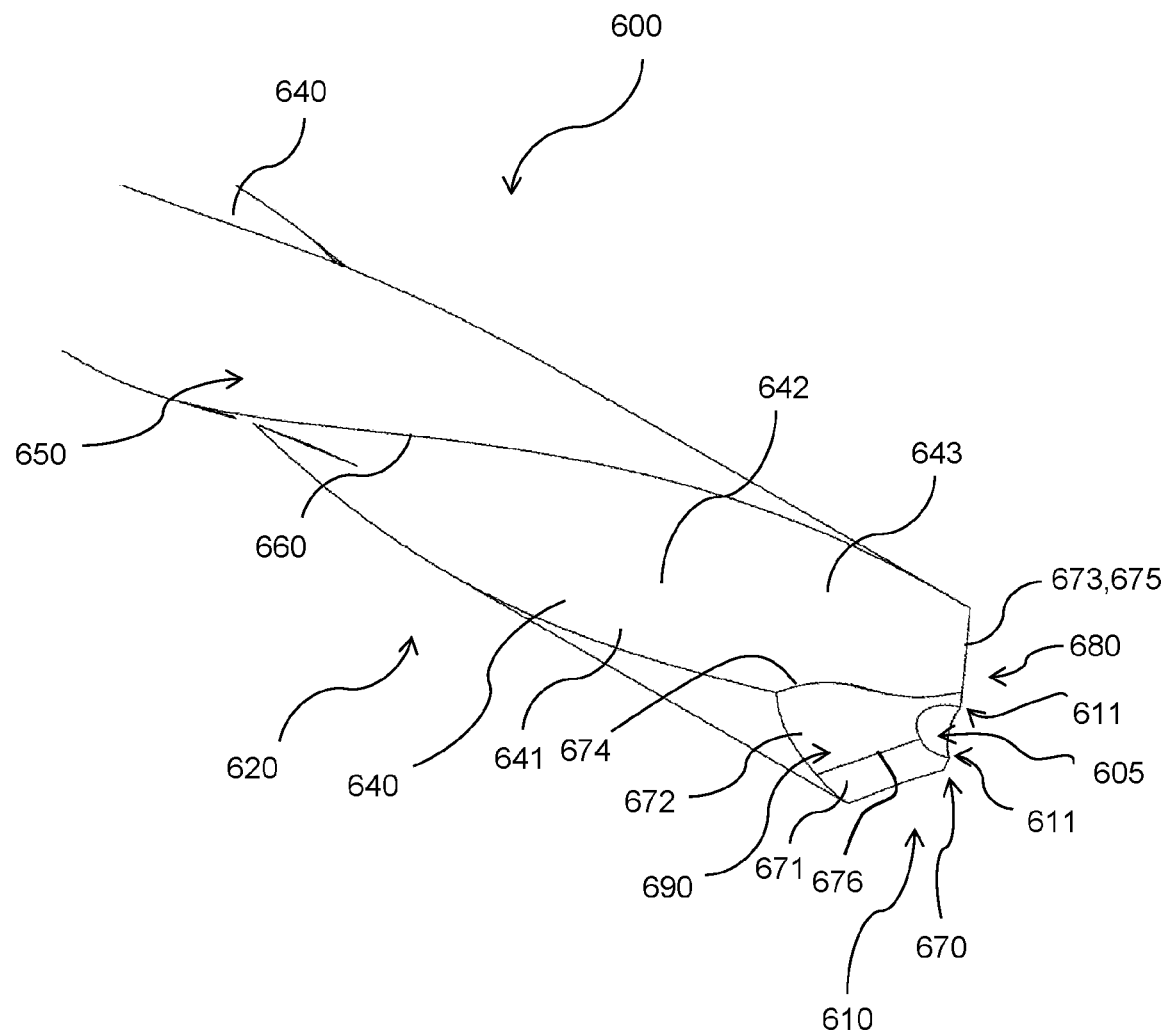
FIG. 27 is an enlarged perspective view of the tip of the drill bit of FIG. 26.
Figure 29:
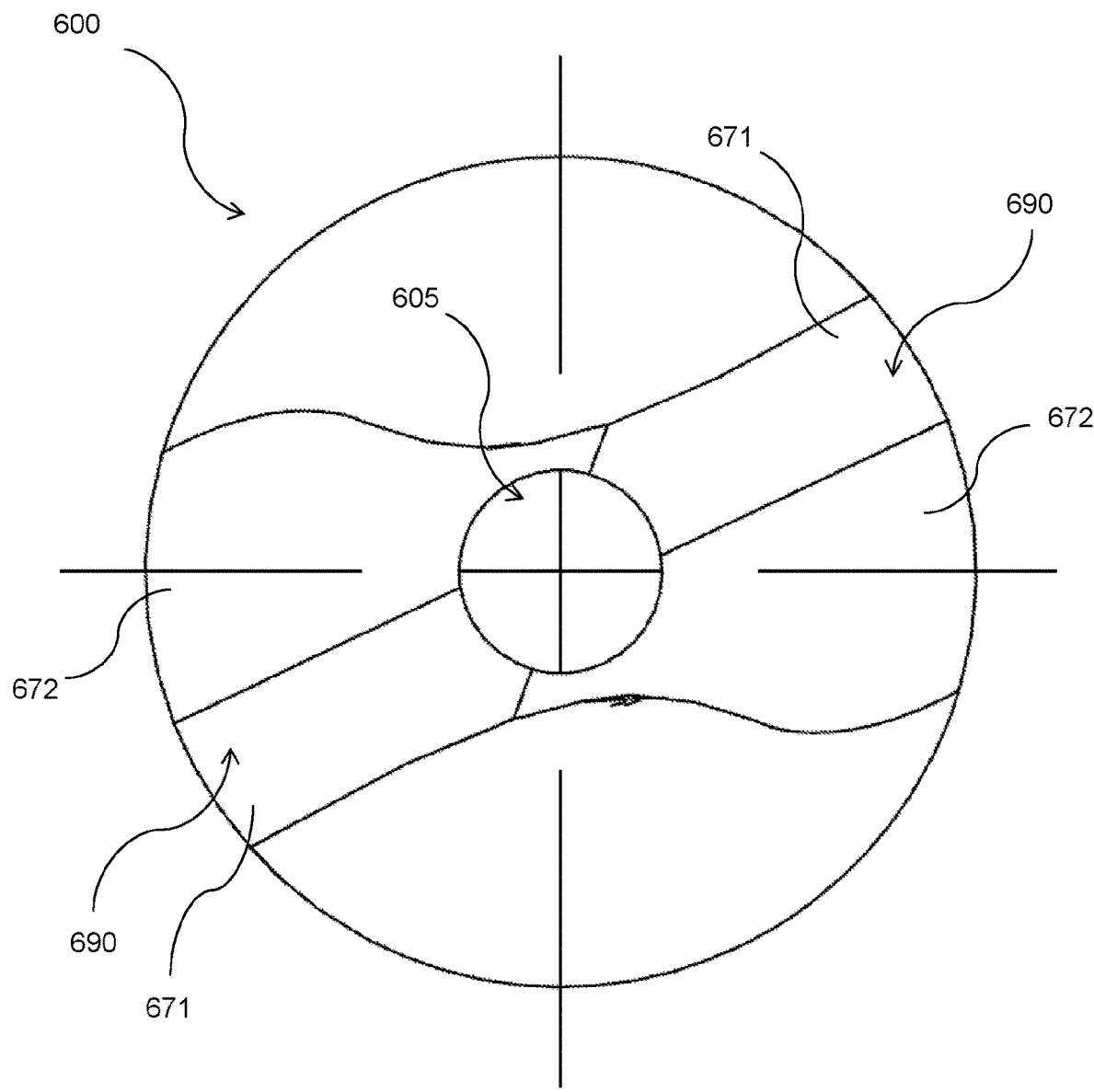
FIG. 29 is an enlarged end elevation view of the drill bit of FIG. 26.

As with the fifth embodiment, each tip face 690 comprises a leading primary facet 671 and a trailing secondary facet 672 inclined relative to the primary facet 671 as best depicted in FIGS. 27 and 29. Each of the primary facets 671 has a tip face leading edge 673 and each of the secondary facets 672 has a tip face trailing edge 674. A tip face intermediate edge 676 is defined at the intersection of the primary facet 671 and the secondary facet 672.

Figure 28:
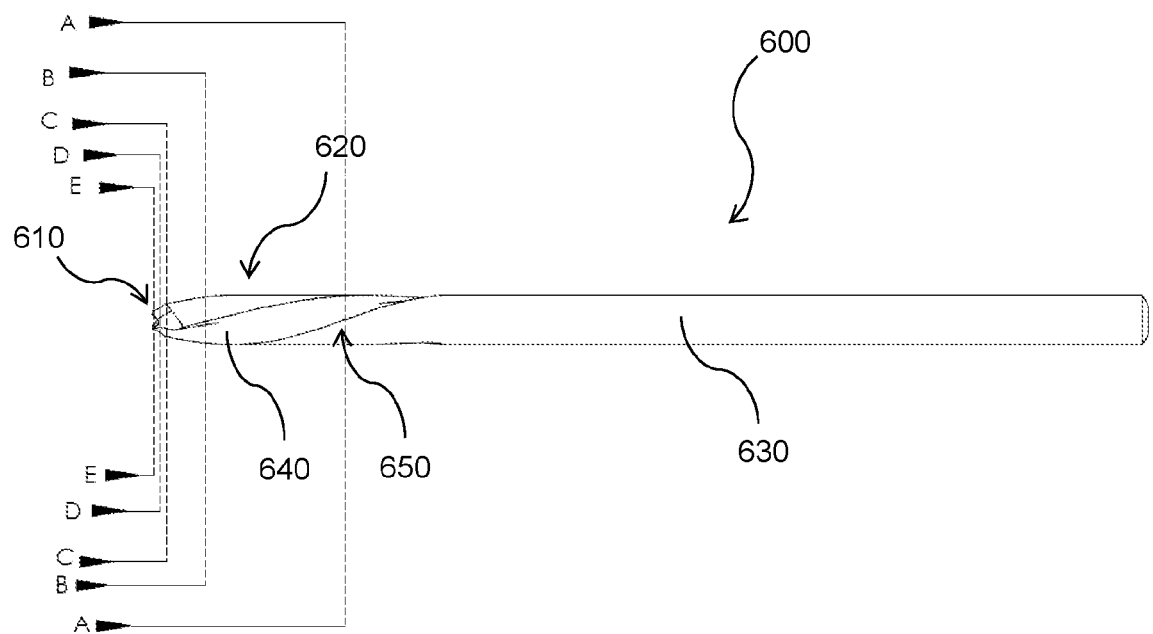
FIG. 28 is a first front elevation view of the drill bit of FIG. 26.
Figures 28A, 28B:
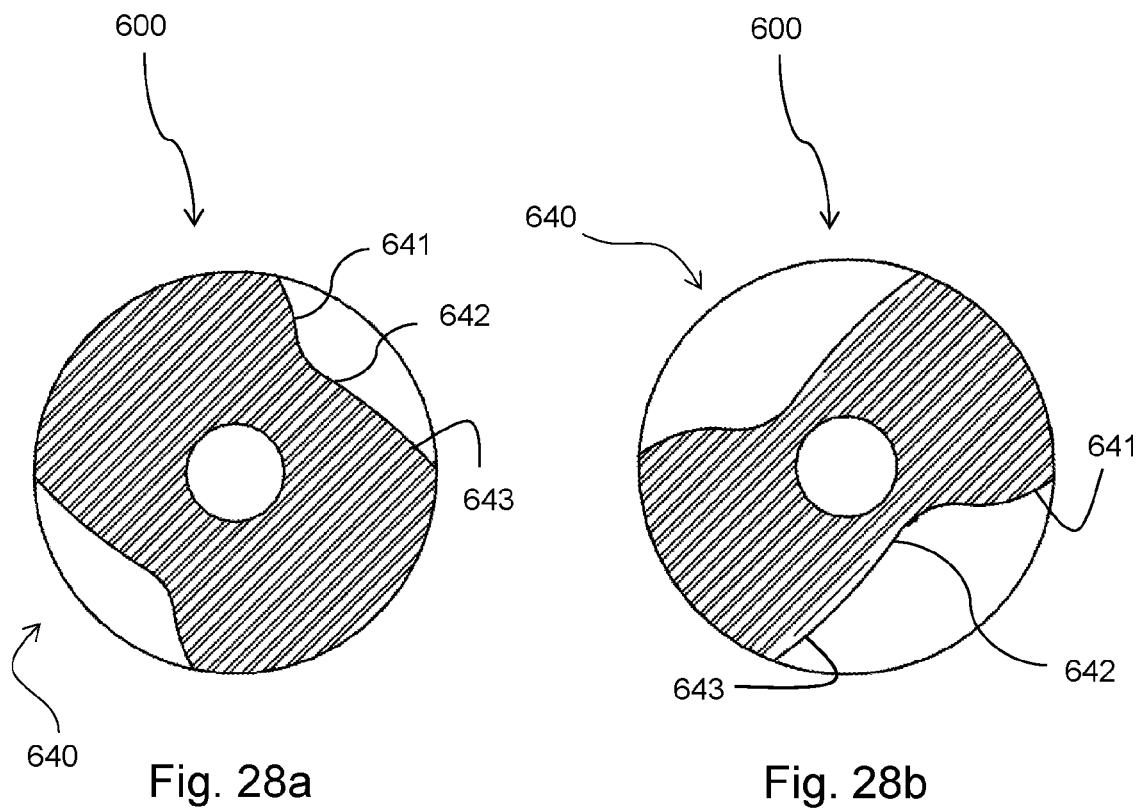
FIGS. 28a through 28e are each cross-sectional views of the drill bit of FIG. 26 taken at sections A-A to E-E of FIG. 28 respectively.
Figure 28C:
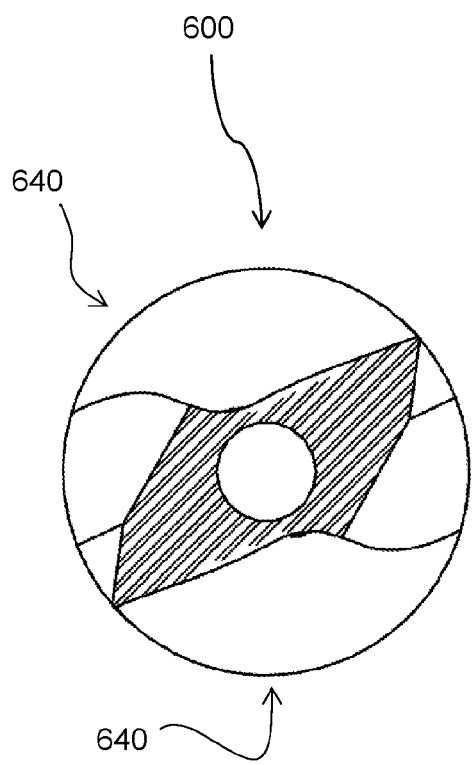
Figure 28D:
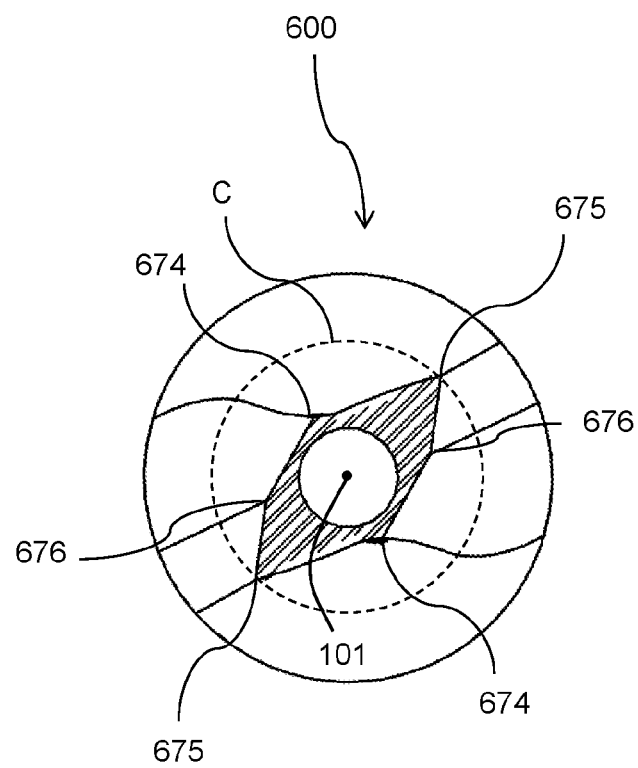
Figure 28E:
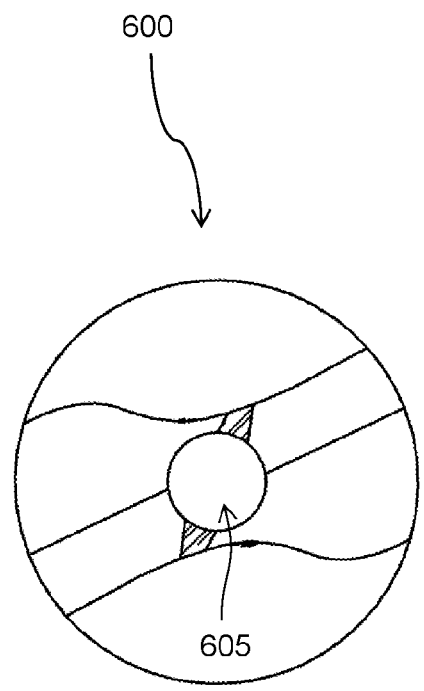

Each of the tip faces 690, at the tip face leading edge 673 of the primary facet 671, forms an intersection with an adjacent flute 640 to define a primary cutting edge 675. In substantially any tip cross-sectional plane extending perpendicular to the axis 101 through the primary cutting edges 675 (as best depicted in the cross-sectional view of FIG. 28*d*), each of the primary cutting edges 675 lies on the circle C extending about the axis 101 and each of the tip face trailing edges 674 and each of the tip face intermediate edges 676 lies entirely within the circle C.

In contrast to the fifth embodiment, apexes 611 are defined by virtue of the hole 605 extending through each of the primary facets 671 and each of the secondary facets 672 of each of the tip faces 690.

As with the fifth embodiment, each of the tip faces 690 of the drill bit 600 has two regions, being a forward tip face region 670 and a rear tip face region 680 as best depicted in FIG. 27. Each forward tip face region 670 extends from adjacent the end of the flutes 640 to the apexes 611 and constitutes the solid forward ends of the tip 610. Each rear tip face region 680 constitutes the region extending from the forward tip face region 670 to the forward end of the adjacent body land 650. The rear tip face regions 680 are each separated by one of the flutes 640. Each of the primary facets 671 and each of the secondary facets 672 extend along the rear tip face region 680 and the forward tip face region 670 to the apexes 611. In this regard, the forward tip face region 670 defines a pair of substantially pyramidal arrangements of the forward extremity of the tip 610.

In this embodiment, the diameter of the drill bit 600 can be larger than the diameter of the drill bit 500. In particular, the diameter of the drill bit 600 could be up to 8 mm or 9 mm or more, depending on the implant to follow into the prepared cavity.

It will be appreciated that the drill bit 600 according to the sixth embodiment operates in substantially the same manner as the drill bit 500 according to the fifth embodiment.

It will also be appreciated that an equivalent hole 605 can be formed in any one of the drill bits 100, 200, 300, 400 and 500 of the first, second, third, fourth and fifth embodiments.

A person skilled in the art will appreciate that various modifications to the drill bit described may be made without departing from the scope of the disclosure of the present specification.

The invention claimed is:

1. A drill bit having a longitudinal axis and to be rotated about said axis in a drilling direction to perform a drilling operation, said drill bit comprising:
a body having a longitudinal length with a proximal end and a distal end, said body having a diameter;
a tapered tip extending from said proximal end and terminating in an apex at an end of said drill bit;
a plurality of flutes, each flute extending helically along said body towards said tip in an opposite direction to said drilling direction;
a land between each of said flutes and extending to said tip;
a plurality of tip faces on said tip and extending from a corresponding land to said apex, each of said tip faces having a tip face leading edge and a tip face trailing edge, each of said tip face leading edges forming an intersection with an adjacent one of said flutes to provide a plurality of primary cutting edges; and wherein
in a tip cross-sectional plane extending perpendicular to said axis through each of said primary cutting edges, each of said primary cutting edges lies on a circle extending about said axis and each of said tip face trailing edges lies entirely within said circle.

2. The drill bit of claim 1, wherein a negative rake angle is defined at each said primary cutting edge.

3. The drill bit of claim 1, wherein each of said flutes have a volume, the total volume of each of said flutes being between about 55 to 65 percent of a volume of a solid cylinder having a diameter equal to the diameter of said body and a length equal to the longitudinal length of said body over which each of said flutes extend.

4. The drill bit of claim 1, wherein the length of each of said flutes is about 5 to 10 times the diameter of said body.

5. The drill bit of claim 1, wherein each of said tip faces is substantially planar.

6. The drill bit of claim 1, wherein each of said tip faces is concavely curved about said axis towards said drilling direction.

7. The drill bit of claim 1, wherein each of said tip faces comprises a forward tip face region extending from adjacent an end of each of said flutes to said apex and a rear tip face region extending from said forward tip face region to an adjacent said land, said second tip face region being separated by each of said flutes, wherein each of said tip faces extend along said rear tip face region and said forward tip face region to said apex, such that each of said tip faces meet at said apex to define a substantially pyramidal arrangement of a forward extremity of said tip.

8. The drill bit of claim 7, wherein each of said tip faces comprises a primary facet extending along said rear tip face region and said forward tip face region to said apex and a secondary facet inclined relative to said primary facet and extending along said rear tip face region and said forward tip face region to said apex, such that said secondary facet and said primary facet meet at said apex to define said pyramidal arrangement of said forward extremity of said tip.

9. The drill bit of claim 1, wherein said drill bit has two flutes.

10. The drill bit of claim 9, wherein, in a cross-sectional plane extending perpendicular to said axis through said body adjacent said tip, each of said flutes subtends an arc of between about 125 to 135 degrees measured at a radially outer periphery of each of said flutes.

11. The drill bit of claim 1, wherein said drill bit has three flutes.

12. The drill bit of claim 11, wherein, in a cross-sectional plane extending perpendicular to said axis through said body adjacent said tip, each of said flutes subtends an arc of between about 100 to 110 degrees measured at a radially outer periphery of each of said flutes.

13. The drill bit of claim 1, wherein said drill bit further comprises a hole extending longitudinally about said axis from one end of said drill bit to the other end of said drill bit, said hole being configured to receive a guide wire for positioning said drill bit.

14. The drill bit of claim 1, wherein said drilling direction is a clockwise direction when viewed from said distal end toward said proximal end.

15. The drill bit of claim 1, wherein said drill bit is an orthopaedic drill bit.

* * * * *